(12) United States Patent
Hayashi

(10) Patent No.: US 8,933,418 B2
(45) Date of Patent: Jan. 13, 2015

(54) SAMPLE OBSERVATION APPARATUS

(75) Inventor: Shinichi Hayashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 395 days.

(21) Appl. No.: 13/541,174

(22) Filed: Jul. 3, 2012

(65) Prior Publication Data
US 2013/0015366 A1 Jan. 17, 2013

(30) Foreign Application Priority Data
Jul. 11, 2011 (JP) .................................. 2011-153133

(51) Int. Cl.
*G01N 21/64* (2006.01)

(52) U.S. Cl.
CPC .................................. *G01N 21/6458* (2013.01)
USPC ..................................... 250/458.1; 250/459.1

(58) Field of Classification Search
USPC ............................................ 250/458.1, 459.1
See application file for complete search history.

(56) References Cited

U.S. PATENT DOCUMENTS

| | | | |
|---|---|---|---|
| 6,166,853 A | 12/2000 | Sapia et al. | |
| 6,219,320 B1 * | 4/2001 | Amada et al. | ................. 369/59.1 |
| 7,227,112 B2 | 6/2007 | Storz | |
| 7,649,682 B2 | 1/2010 | Olschewski | |
| 7,710,469 B2 * | 5/2010 | Ueyama | ..................... 348/240.2 |
| 7,863,552 B2 * | 1/2011 | Cartlidge et al. | ........... 250/208.1 |
| 2002/0126732 A1 * | 9/2002 | Shakouri et al. | .............. 374/130 |
| 2002/0159058 A1 * | 10/2002 | Weiner | .......................... 356/318 |
| 2005/0031182 A1 * | 2/2005 | Inoue | ............................. 382/132 |
| 2007/0139541 A1 * | 6/2007 | Fein et al. | ...................... 348/294 |
| 2009/0201579 A1 | 8/2009 | Shibata | |
| 2009/0294694 A1 * | 12/2009 | Lippert | ...................... 250/461.1 |
| 2010/0074486 A1 | 3/2010 | Broser et al. | |
| 2010/0327183 A1 * | 12/2010 | Baltz et al. | ................. 250/458.1 |
| 2012/0081535 A1 * | 4/2012 | Hayashi | .......................... 348/79 |

FOREIGN PATENT DOCUMENTS

JP 2008-107557 A 5/2008

OTHER PUBLICATIONS

T. Wilson et al; "Theory and Practice of Scanning Optical Microscopy", Academic Press 1984; Chapter 6, Section 6; pp. 152-156.

* cited by examiner

Primary Examiner — Christine Sung
(74) Attorney, Agent, or Firm — Holtz, Holtz, Goodman & Chick PC

(57) ABSTRACT

A sample observation apparatus includes excitation light irradiation unit to irradiate sample with excitation light; excitation light modulator to modulate spatial intensity distribution of the excitation light on the sample; excitation light modulation control unit to control the excitation light modulator according to modulation control signal; photo detection unit to detect light emission from the sample and to generate a detection signal; image generation unit to generate image data of the sample according to the modulation control signal and the detection signal; modulation control signal generation unit to generate the modulation control signal such that Nyquist frequency of the image data will be larger than cut-off frequency in the spatial intensity distribution of the excitation light on the sample; and image processing unit to emphasize high-frequency component that exceeds the cut-off frequency included in the image data.

20 Claims, 15 Drawing Sheets

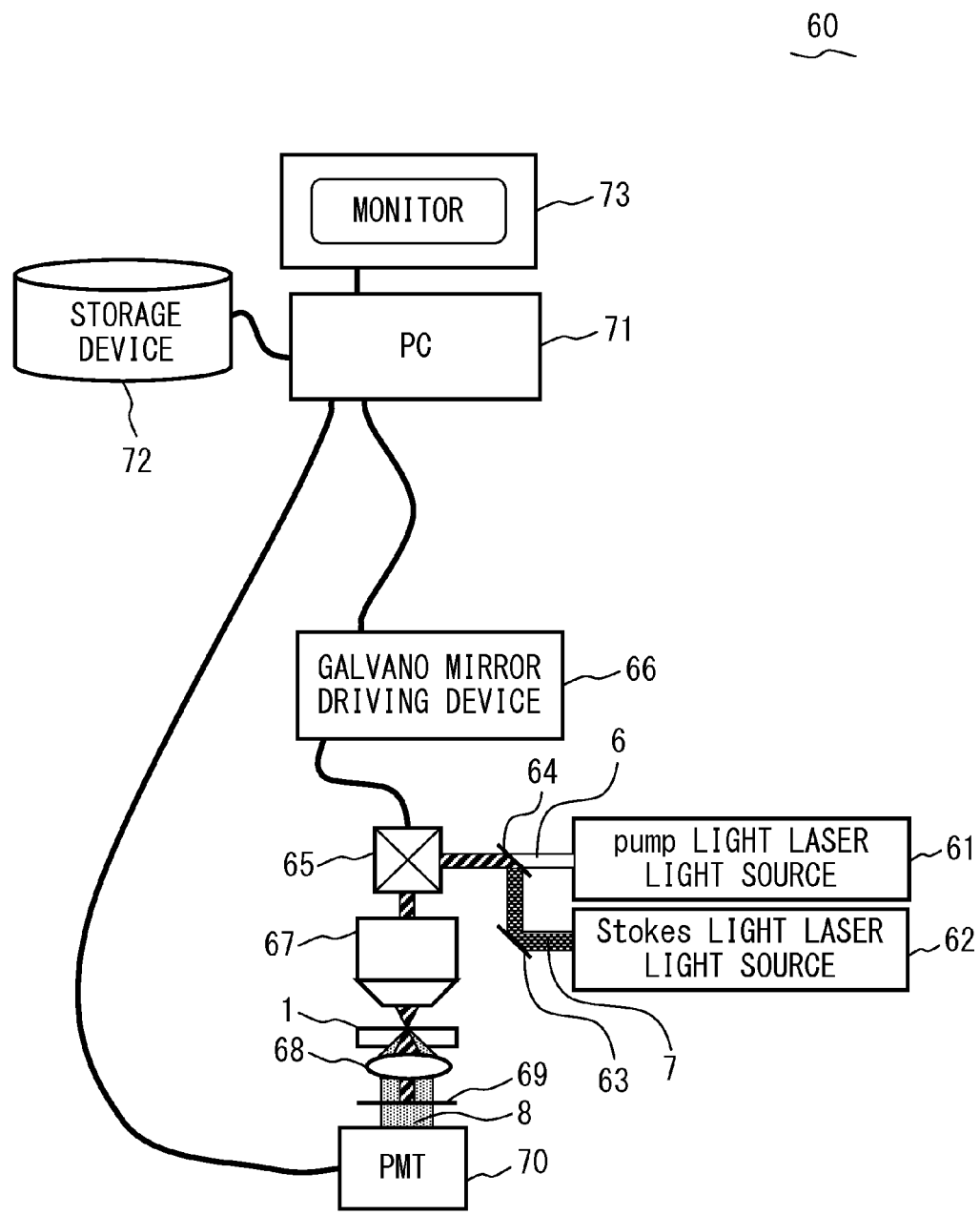
F I G. 1 4

SAMPLE OBSERVATION APPARATUS

CROSS REFERENCE TO RELATED APPLICATIONS

This application is based upon and claims the benefit of priority from prior Japanese Patent Application No. 2011-153133, filed Jul. 11, 2011, the entire contents of which are incorporated herein by this reference.

BACKGROUND OF THE INVENTION

1. Field of the Invention

The present invention relates to a sample observation apparatus, and in particular, relates to a sample observation apparatus that generates a sample image in which a super-resolution component is visualized.

2. Description of the Related Art

In scanning microscopes, light that is condensed to one spot on a sample is moved by a scanning unit such as a galvano mirror to scan the sample, and thereby the sample is observed. Such scanning microscopes are widely used in several technical fields, and are disclosed, for example, in U.S. Pat. No. 7,227,112 and U.S. Pat. No. 7,649,682.

As disclosed in U.S. Pat. No. 7,227,112, in scanning microscopes, there are several items to be set, such as pinhole diameter, the voltage of a PMT, the output intensity or wavelength of a light source, or scanning speed, and the image quality may vary greatly depending on these items to be set. For example, in fluorescence laser scanning microscopes (hereinafter referred to as a fluorescence LSM), if a pinhole diameter is made to be sufficiently smaller than an Airy disk diameter, it is known that a resolution exceeding the cut-off frequency of an optical system (hereinafter, referred to as superresolution) is obtained. Such techniques are disclosed, for example, in T. Wilson and C. Sheppard, "Theory and Practice of Scanning Optical Microscopy", Academic Press, 1984, Chapter 6, Section 6.

A main object of conventional fluorescence LSMs is not to obtain a super-resolution component, but to achieve a sectioning effect. If the pinhole diameter is downsized with reference to the Airy disk diameter in order to obtain a super-resolution component, the amount of fluorescent light detected by a detector may decrease.

For this reason, in conventional fluorescence LSMs, the detection efficiency is prioritized, and the pinhole aperture diameter is generally set to a diameter on the order of the Airy disk diameter.

Fluorescence LSMs have been described in the above, but microscopes in which a super-resolution component is detected are not limited to the fluorescence LSMs. In scanning microscopes, an illumination light is condensed to one spot on a sample, and the spot to which the illumination light is condensed is moved by a scanning unit. Accordingly, the illumination light is modulated spatially or temporally. Hence, a super-resolution component may be detected in scanning microscopes as a whole.

SUMMARY OF THE INVENTION

It is an object in one aspect of the invention to provide a sample observation apparatus including: an excitation light irradiation unit to irradiate a sample with an excitation light; an excitation light modulation unit to modulate a spatial intensity distribution of the excitation light on the sample; an excitation light modulation control unit to control the excitation light modulation unit according to a modulation control signal; a photo detection unit to detect light emission from the sample caused by irradiation with the excitation light to generate a detection signal; an image generation unit to generate image data of the sample according to the modulation control signal and the detection signal; a modulation control signal generation unit to generate the modulation control signal such that a Nyquist frequency of the image data will be larger than a cut-off frequency in the spatial intensity distribution of the excitation light on the sample; and an image processing unit to emphasize a high-frequency component that exceeds the cut-off frequency included in the image data.

BRIEF DESCRIPTION OF THE DRAWINGS

The present invention will be more apparent from the following detailed description when the accompanying drawings are referenced.

FIG. 14 illustrates an example of the configuration of a coherent anti-Stokes Raman scattering (CARS) microscope according to the Fourth Embodiment.

DESCRIPTION OF THE PREFERRED EMBODIMENTS

Figure 1:
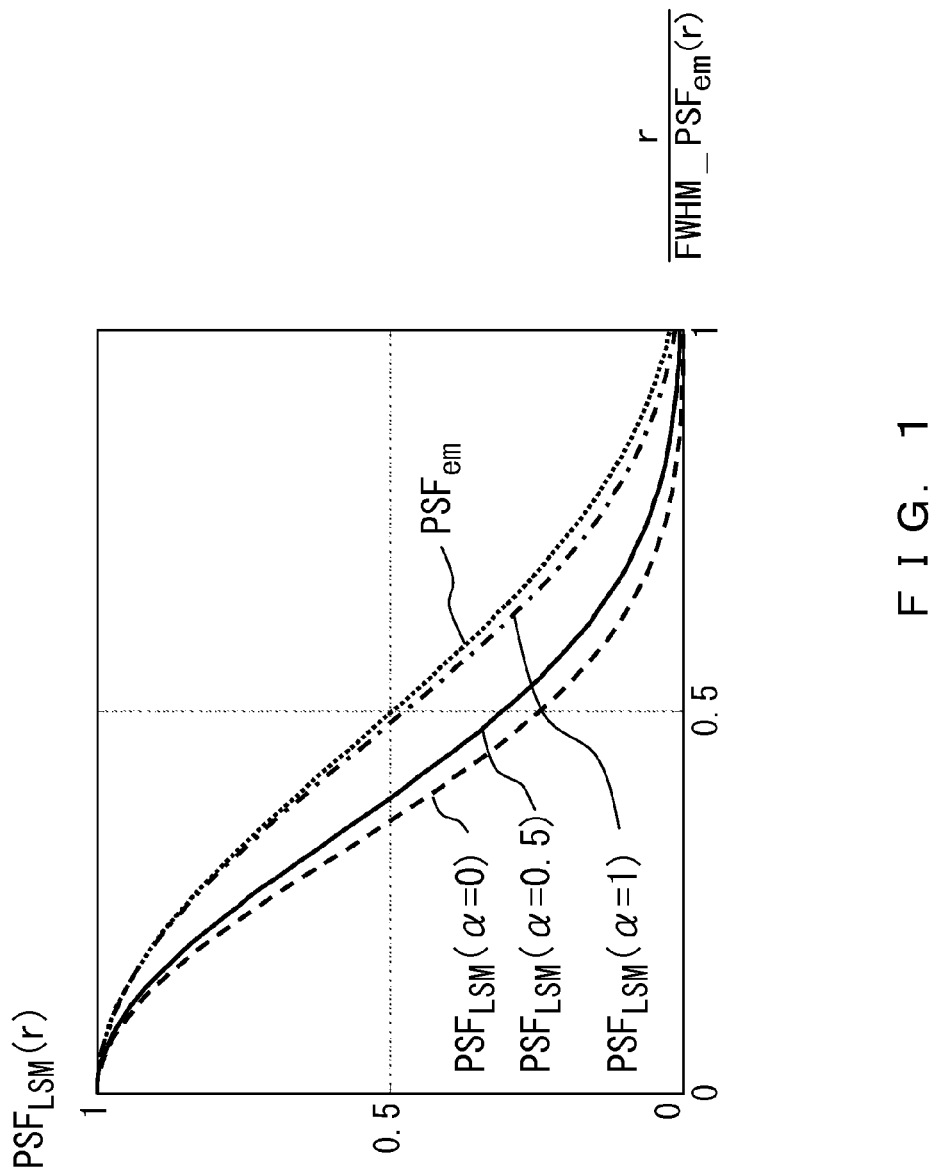
FIG. 1 illustrates an example of the Point Spread Functions of a fluorescence LSM.

Before describing embodiments of the present invention, firstly, the image-forming characteristics of a fluorescence LSM will be described.

The image-forming formula of a fluorescence LSM is expressed in equations (1) and (2) below.

$$PSF_{LSM}(r) = PSF_{ex}(r) \times \{PSF_{em}(r) \otimes PH(r)\} \quad (1)$$

$$MTF_{LSM}(f) = MTF_{ex}(f) \otimes \{MTF_{em}(f) \times \tilde{PH}(f)\} \quad (2)$$

(where, $\otimes$ indicates convolution operator)

In equations (1) and (2) above, $PSF_{LSM}$ and $MTE_{LSM}$ indicate a Point Spread Function (PSF) that indicates the image-forming characteristics of a fluorescence LSM and a Modulation Transfer Function (MTF) that is obtained by performing Fourier transformation on the Point Spread Function, respectively. $PSF_{ex}$ and $MTF_{ex}$ indicate a Point Spread Function of the excitation light spot on a sample and a Modulation Transfer Function that is obtained by performing Fourier transformation on the Point Spread Function, respectively, both of which indicate the light condensing characteristics when the excitation light is condensed onto a sample plane. $PSF_{em}$ and $MTF_{em}$ indicate a Point Spread Function of the detection wavelength on a sample plane and a Modulation Transfer Function that is obtained by performing Fourier transformation on the Point Spread Function, respectively, both of which indicate the image-forming characteristics when the fluorescent light from the sample plane forms an image on an image plane (confocal plane). "PH" and "~PH" indicate a function obtained by projecting the transmission function of a confocal stop onto a sample and a function obtained by performing Fourier transformation on the obtained function of "PH", respectively. "r" is the distance from the optical axis, and indicates space coordinate of the sample position. "f" is a spatial frequency coordinate conjugates to "r".

Moreover, Point Spread Functions $PSF_{ex}$ and $PSF_{em}$, Modulation Transfer Functions $MTF_{ex}$ and $MTF_{em}$, and functions "PH" and "~PH" are expressed in equations (3), (4), (5), (6), (7), and (8), respectively, in an approximate manner. Note that equations (7) and (8) are applied when the aperture of a confocal stop is in a pinhole shape (circle shape).

$$PSF_{ex}(r) = jinc^2(f_{c,ex}r) \quad (3)$$

$$PSF_{em}(r) = jinc^2(f_{c,em}r) \quad (4)$$

$$MTF_{ex}(f) = chinesehat\left(\frac{f}{f_{c,ex}}\right) \quad (5)$$

$$MTF_{em}(f) = chinesehat\left(\frac{f}{f_{c,em}}\right) \quad (6)$$

$$PH(r) = \begin{cases} 1 & \left(|r| < \frac{d_{PH}}{2M_{ob}}\right) \\ 0 & (else) \end{cases} \quad (7)$$

$$\tilde{PH}(f) = jinc\left(\frac{d_{PH}}{2M_{ob}}f\right) \quad (8)$$

In the equations above, $f_{c,ex}$ and $f_{c,em}$ indicate a cut-off frequency in the spatial intensity distribution (upper limit to spatial frequency) of the excitation light of an excitation wavelength $\lambda_{ex}$ on a sample as well as a cut-off frequency in the spatial intensity distribution (upper limit to spatial frequency) of the fluorescent light image of a detection wavelength $\lambda_{em}$ corresponds on a sample plane, respectively, and are expressed in equations (9) and (10) below. NA, $d_{PH}$, and $M_{ob}$ indicate the numerical aperture of an objective lens on a sample side, the aperture diameter of a confocal stop, and the projection magnification between a sample plane and a confocal stop, respectively. A Jinc function and a chinesehat function are expressed in equations (11) and (12) below. $J_1$ is a Bessel function of the first kind.

$$f_{c,ex} = \frac{2NA}{\lambda_{ex}} \quad (9)$$

$$f_{c,em} = \frac{2NA}{\lambda_{em}} \quad (10)$$

$$jinc(s) \equiv \frac{2J_1(\pi s)}{\pi s} \quad (11)$$

$$chinesehat(s) \equiv \begin{cases} \frac{2}{\pi}\{\cos^{-1}(s) - s\sqrt{1-s^2}\} & (|s| < 1) \\ 0 & (else) \end{cases} \quad (12)$$

Figure 2:
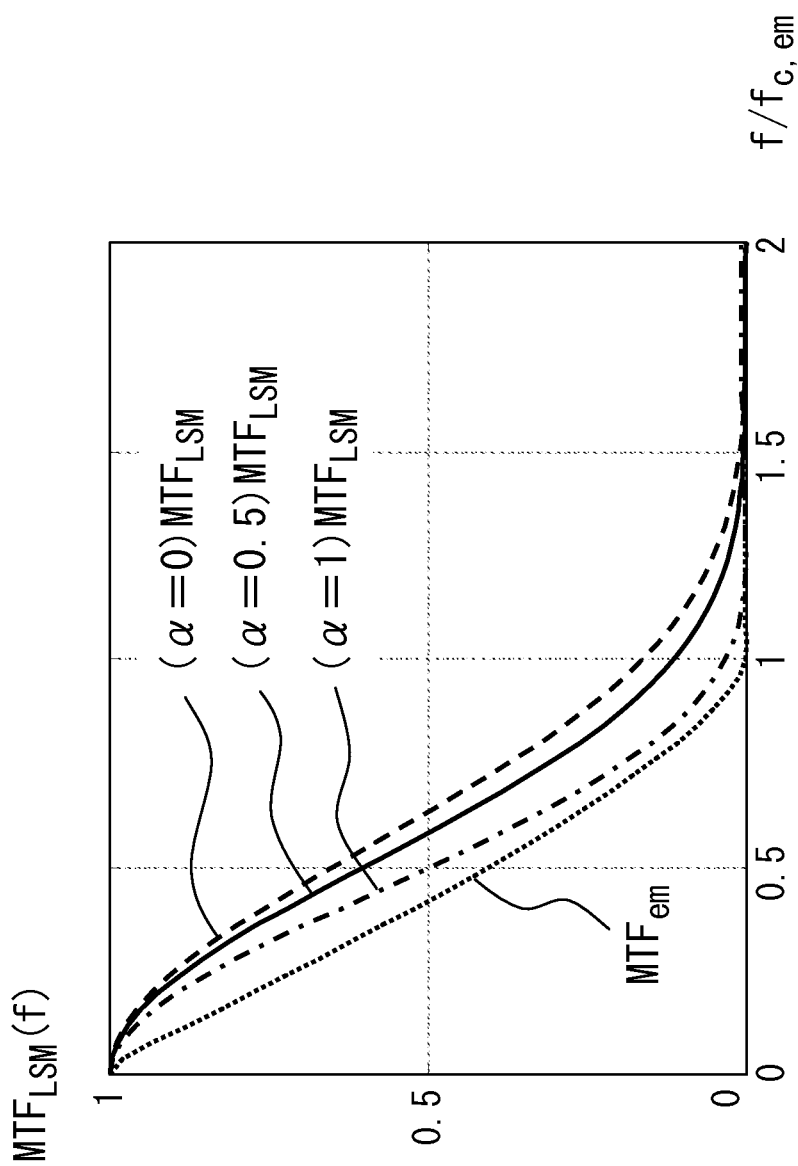
FIG. 2 illustrates an example of the Modulation Transfer Functions of a fluorescence LSM.
Figure 3:
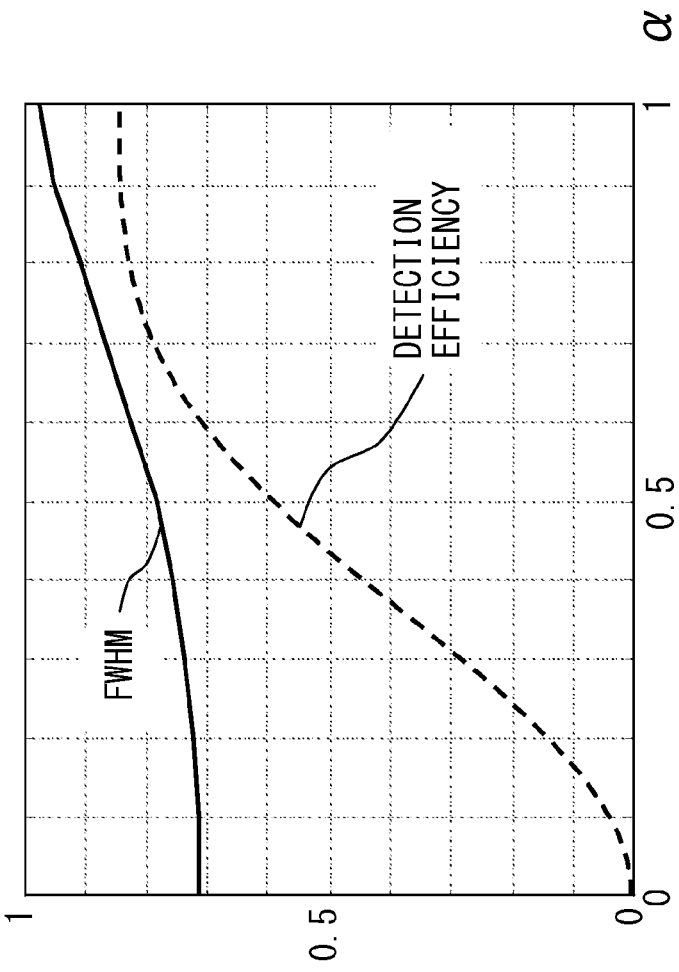
FIG. 3 is a diagram in which, in regard to the Full Width Half Maximum (FWHM) of a Point Spread Function and detection efficiency, a fluorescence LSM is compared with a wide-field fluorescence microscope.

FIG. 1 illustrates an example of the Point Spread Functions of a fluorescence LSM, and a Point Spread Function $PSF_{em}$ and a plurality of Point Spread Functions $PSF_{LSM}$ of which the settings of the confocal stops are different from each other are illustrated therein. The horizontal axis in FIG. 1 indicates the distance from the optical axis "r/FWHM_$PSF_{em}$(r)", and this distance is normalized by the Full Width Half Maximum (FWHM) of a Point Spread Function $PSF_{em}$. FIG. 2 illustrates an example of the Modulation Transfer Functions of a fluorescence LSM, and a Modulation Transfer Function $MTF_{em}$ and a plurality of Modulation Transfer Functions $MTF_{LSM}$ in which the settings of the confocal stops are different from each other are illustrated therein. The horizontal axis in FIG. 2 indicates a spatial frequency $f/f_{c,em}$ that is normalized by a cut-off frequency $f_{c,em}$. In FIG. 1 and FIG. 2, cases are illustrated in which the ratio α of the aperture diameter of a confocal stop to the Airy disk diameter formed by a fluorescent light on a confocal stop is set to 0, 0.5, and 1. FIG. 3 is a diagram in which a fluorescence LSM is compared with a wide-field fluorescence microscope about the Full Width Half Maximum (FWHM) and detection efficiency of a Point Spread Function. The horizontal axis indicates the aforementioned ratio α of the aperture diameter of a confocal stop to the Airy disk diameter, and the vertical axis indicates a ratio of the Full Width Half Maximum (FWHM) of the Point Spread Function of a fluorescence LSM with reference to that of a wide-field fluorescence microscope or detection efficiency. Here, a wide-field fluorescence microscope indicates a fluorescence microscope in which a sample plane is evenly irradiated, and also relates to a non-confocal microscope.

The image-forming characteristics of a fluorescence LSM are dependent on the modulation performed by a fluorescence LSM on an excitation light and fluorescent light, respectively, as illustrated in equations (1) and (2). Note that the modulation on a fluorescent light includes not only the modulation by an optical system but also the modulation by a confocal stop. On the other hand, the image-forming characteristics of a wide-field fluorescence microscope are determined by the modulation on a fluorescent light performed by an optical system. This is because in a wide-field fluorescence microscope, modulation by an optical system on an excitation light (a process of condensing an excitation light to a sample plane) is not performed and modulation by a confocal stop on a fluorescent light is not performed. In other words, the Point Spread Function $PSF_{em}$ and Modulation Transfer Function $MTF_{em}$ that are illustrated in FIG. 1 and FIG. 2 correspond to the Point Spread Function and Modulation Transfer Function of a wide-field fluorescence microscope, respectively.

As illustrated in FIG. 1, compared with the Point Spread Function $PSF_{em}$, the Point Spread Function $PSF_{LSM}$ has characteristics in which more lights are distributed at a position close to an optical axis ($r/FWHM\_PSF_{em}(r)=0$). Moreover, as illustrated in FIG. 2, compared with the Modulation Transfer Function $MTF_{em}$, the Modulation Transfer Function $MTF_{LSM}$ is distributed to wider spatial frequencies. These facts indicate that a fluorescence LSM has an image-forming capability higher than that of a wide-field fluorescence microscope, and that a fluorescence LSM is capable of detecting a higher frequency component. Moreover, as illustrated in FIG. 1 and FIG. 2, the smaller the ratio α is set, the higher frequency component a fluorescence LSM may detect.

On the other hand, as illustrated in FIG. 2, in a fluorescence LSM where the ratio α is 1, only a few super-resolution components that exceed the cut-off frequency of a wide-field fluorescence microscope are transmitted. If the ratio α is made small in order to transmit a super-resolution component more efficiently, as illustrated in FIG. 3, a detection efficiency significantly decreases as the Full Width Half Maximum (FWHM) of a Point Spread Function is reduced. For this reason, the generated image data tends to display the image of a sample very darkly. Accordingly, in any case, it is almost impossible to recognize the detected super-resolution component on a display, and a super-resolution component cannot be visualized.

As discussed above, conventional fluorescence LSMs may detect a super-resolution component, but the strength of the detected super-resolution component is very weak. Hence, conventional fluorescence LSMs do not successfully visualize a super-resolution component. The same can be said for scanning microscopes in general.

Some embodiments of the present invention will be described below in detail.

First Embodiment

Figure 4:
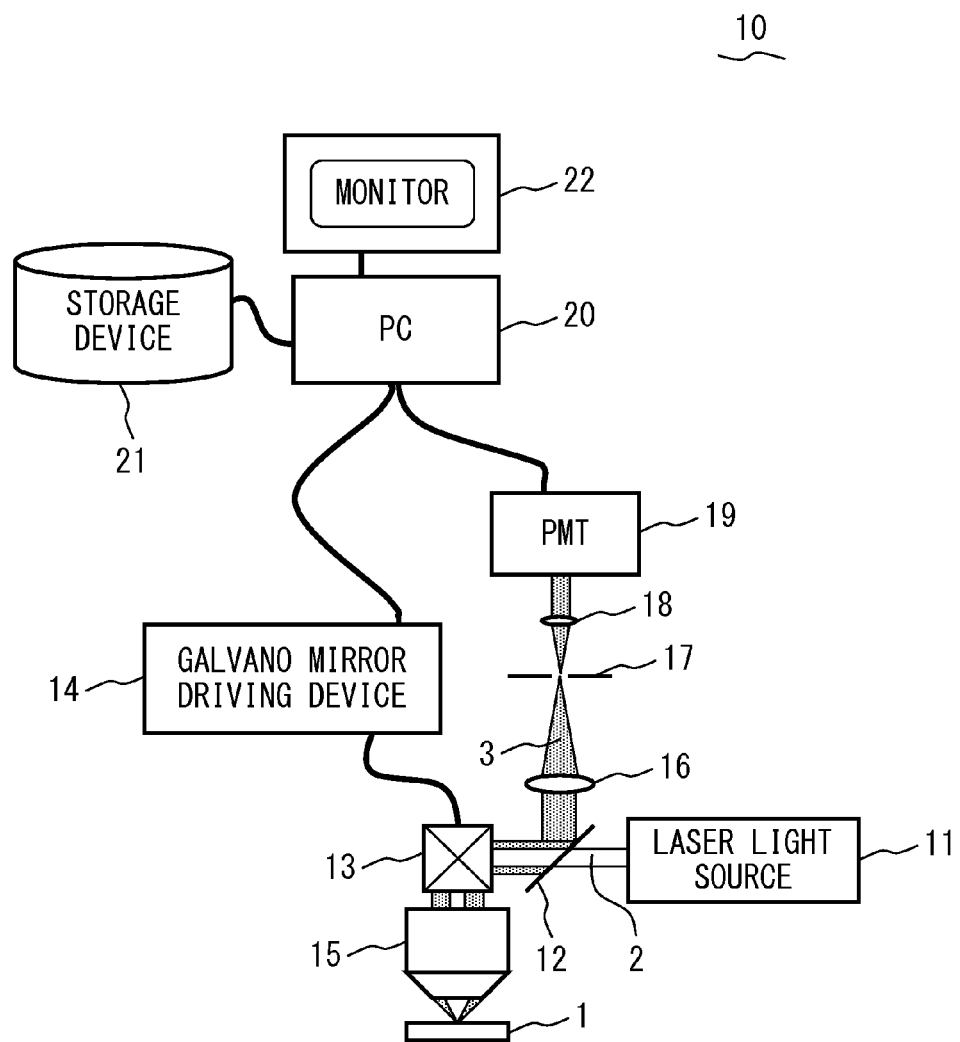
FIG. 4 illustrates an example of the configuration of a fluorescence LSM according to the First Embodiment.

FIG. 4 illustrates an example of the configuration of a fluorescence LSM according to the First Embodiment. A fluorescence LSM 10 that is illustrated in FIG. 4 is a sample observation apparatus that generates a superresolution image on which a super-resolution component is visualized. The fluorescence LSM 10 includes: a laser light source 11 that emits an excitation light 2; a dichroic mirror 12 that allows the excitation light 2 to pass through and that reflects a fluorescent light 3 from a sample 1; a galvano mirror 13 that scans the sample 1; a galvano mirror driving device 14 that drives the galvano mirror 13 according to a modulation control signal; an objective lens 15 that condenses the excitation light 2 onto the sample 1; a lens 16; a confocal stop 17 that configures a pinhole (aperture) at an optically conjugate position with the position to which the objective lens 15 condenses the excitation light 2; a lens 18; a PMT detector 19 that detects the fluorescent light 3 to generate a detection signal; a PC 20 that generates the image data of the sample 1 according to a modulation control signal and a detection signal; a storage device 21 that stores the image data of the sample 1; and a monitor 22 that displays the image data of the sample 1.

In the fluorescence LSM 10 according to the First Embodiment, the excitation light 2 emitted from the laser light source 11 passes through the dichroic mirror 12, and enters the objective lens 15 through the galvano mirror 13. As the objective lens 15 condenses the excitation light 2 onto the sample 1, the sample 1 is irradiated with the excitation light 2. In other words, in the fluorescence LSM 10, the laser light source 11, the dichroic mirror 12, the galvano mirror 13, and the objective lens 15 configure an excitation light irradiation unit that irradiates the sample 1 with the excitation light 2, and the objective lens configures a light condensing unit that condenses the excitation light 2 onto the sample 1. The objective lens 15 that functions as a light condensing unit may effectively increase the cut-off frequency in the spatial intensity distribution of the excitation light 2 on the sample 1.

The position to which the excitation light 2 is condensed moves on an XY plane that is orthogonal to the optical axis as the galvano mirror driving device 14 drives the galvano mirror 13 according to a modulation control signal from the PC 20. In other words, in the fluorescence LSM 10, the galvano mirror 13 configures an excitation light modulation unit that modulates the spatial intensity distribution of the excitation light 2 on the sample 1, and also configures a scanning unit that moves a position to which the objective lens 15 condenses the excitation light 2 to scan the sample 1. Moreover, the galvano mirror driving device 14 configures an excitation light modulation control unit that controls the excitation light modulation unit according to a modulation control signal from the PC 20.

On the sample 1 irradiated with the excitation light 2, a fluorescent material existing on the light-condensing position is excited, and the fluorescent light 3 is emitted with an amount of light that linearly depends on the intensity of the irradiation of the sample with the excitation light 2. The fluorescent light 3 travels along the same path as that of the excitation light 2 in the opposite direction, and enters the dichroic mirror 12. After being reflected at the dichroic mirror 12, the fluorescent light 3 is condensed by the lens 16 to enter the confocal stop 17.

At the confocal stop 17, the fluorescent light not caused at the light-condensing position is blocked, and only the fluorescent light 3 caused at the light-condensing position passes through the aperture. Note that due to its confocal effect, the confocal stop 17 contributes to the detection of a frequency component that is higher than the cut-off frequency in the spatial intensity distribution of the excitation light 2 on the sample 1.

Afterward, the fluorescent light 3 enters the PMT detector 19 through the lens 18, and is thereby detected. The PMT detector 19 generates a detection signal according to the amount of light of the detected fluorescent light 3, and transmits the generated detection signal to the PC 20. In other words, in the fluorescence LSM 10, the PMT detector 19 is a photo detection unit that detects the fluorescent light 3 from sample 1 caused by irradiation with the excitation light 2 to generate a detection signal.

The PC 20 generates a modulation control signal such that the Nyquist frequency of image data to be generated will be larger than the cut-off frequency in the spatial intensity distribution of the excitation light 2 on the sample 1, and performs image processing by emphasizing a high-frequency component that exceeds the cut-off frequency in the spatial intensity distribution of the excitation light 2 on the sample 1 included in the generated image data. In other words, in the fluorescence LSM 10, the PC 20 configures an image generation unit that generates the image data of the sample 1 and configures a modulation control signal generation unit that generates a modulation control signal, and also configures an image processing unit that emphasizes a high-frequency component of the image data. The Nyquist frequency is compared with the cut-off frequency in consideration of the projection magnification of the sample image on the image plane. In particular, a converted amount obtained by adjusting one of the Nyquist frequency and the cut-off frequency with the projection magnification is compared with the other one of the Nyquist frequency and the cut-off frequency.

Figure 5:
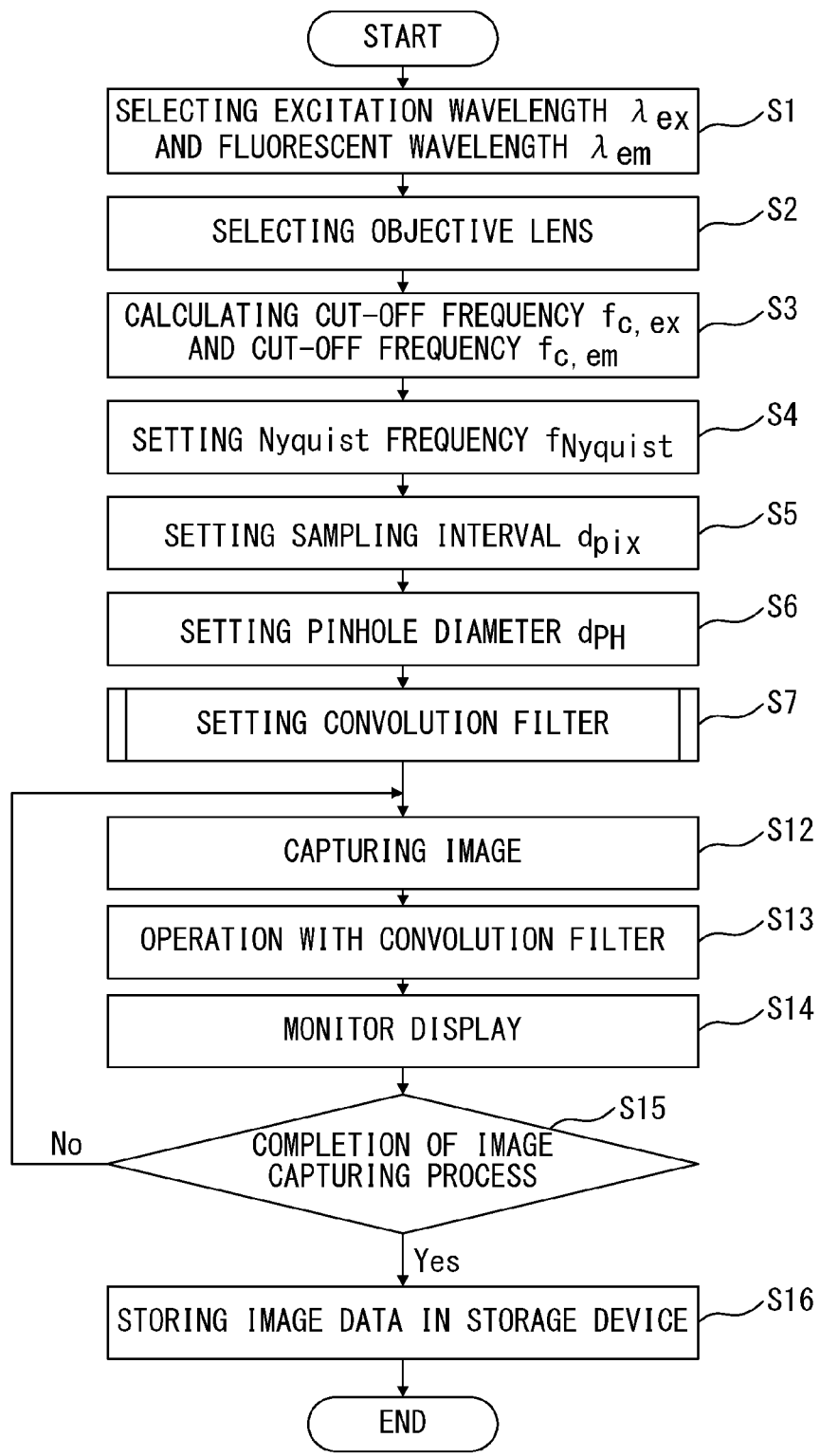
FIG. 5 is a flowchart illustrating the processes in which a fluorescence LSM according to the First Embodiment generates a superresolution image.

FIG. 5 is a flowchart illustrating the processes of generating a superresolution image, which are performed by the fluorescence LSM 10. A method for generating a superresolution image by using the fluorescence LSM 10 will be described with reference to FIG. 5 in a specific manner.

Once the processes of generating a superresolution image are started, firstly, in step S1, a user selects an excitation wavelength $\lambda_{ex}$ and a fluorescent wavelength (detection wavelength) $\lambda_{em}$ to be used for observation, and these excitation wavelength $\lambda_{ex}$ and fluorescent wavelength $\lambda_{em}$ are set to the LSM 10. For example, if the laser light source 11 is an Ar laser and the fluorescent material in the sample 1 is Enhanced Green Fluorescence Protein (EGFP), in step S1, the excitation wavelength and fluorescent wavelength are set to $\lambda_{ex}$=488 nm and $\lambda_{em}$=508 nm, respectively.

In step S2, the user selects the objective lens 15. For example, an objective lens in which the magnification is 100 in combination with the lens 16 and in which the numerical aperture is 1.4 is selected, and $M_{ob}$=100 and NA=1.4 are set to the fluorescence LSM 10.

In step S3, a cut-off frequency $f_{c,ex}$ in the spatial intensity distribution of the excitation light 2 of an excitation wavelength $\lambda_{ex}$ on the sample 1 and a cut-off frequency $f_{c,em}$ in the spatial intensity distribution of the fluorescent light 3 of a detection wavelength $\lambda_{em}$ on the sample 1 are calculated. Here, these cut-off frequencies are calculated as $f_{c,ex}$=5.7 $\mu m^{-1}$ and $f_{c,em}$=5.5 $\mu m^{-1}$, respectively, by using equations (9) and (10).

As indicated in equation (9), the cut-off frequency $f_{c,ex}$ in the spatial intensity distribution of the excitation light 2 on the sample 1 is determined by a diffraction limit that is calculated from a wavelength $\lambda_{ex}$ of the excitation light 2 and a numerical aperture NA on the emitting side (on the sample 1 side) of the objective lens 15.

In step S4, the Nyquist frequency of the image data to being generated by the fluorescence LSM 10 is set. The Nyquist frequency of the image data $f_{Nyquist}$ is set to be larger than the cut-off frequency $f_{c,ex}$ in the spatial intensity distribution of the excitation light 2 on the sample 1 in order to record a super-resolution component. Here, for example, the Nyquist frequency of the image data $f_{Nyquist}$=11.2 $\mu m^{-1}$ calculated by an equation (13) below is set.

$$f_{Nyquist}=f_{c,ex}+f_{c,em} \quad (13)$$

Accordingly, a frequency component on the order of twice the cut-off frequency $f_{c,ex}$ in the spatial intensity distribution of the excitation light 2 on the sample 1 may be recorded.

Here, a Nyquist frequency $f_{Nyquist}$ that is calculated by using equation (13) is set, but the relationship between the Nyquist frequency $f_{Nyquist}$ of the image data and the cut-off frequency $f_{c,ex}$ is not limited to such a relationship. In order to achieve a high superresolution capability, it is desirable that a Nyquist frequency $f_{Nyquist}$ be equal to or larger than 1.5 times the cut-off frequency $f_{c,ex}$. However, if a Nyquist frequency $f_{Nyquist}$ is too large, a reduction in the amount of light or an increase in noise may occur so as to achieve such a large frequency. In order to avoid such a situation, it is desirable that a Nyquist frequency $f_{Nyquist}$ be equal to or smaller than about four times the cut-off frequency $f_{c,ex}$.

In step S5, the sampling intervals at which the galvano mirror 13 scans the sample 1 are set. A value that corresponds to the Nyquist frequency $f_{Nyquist}$ set in step S4 is set to sampling intervals $d_{pix}$. This is because the Nyquist frequency of the image data $f_{Nyquist}$ is determined by the sampling intervals at which the galvano mirror 13 scans the sample 1. In particular, a sampling interval $d_{pix}$ is set to a value calculated by equation (14) below such that the Nyquist frequency $f_{Nyquist}$ will be half the sampling frequency ($f_{pix}=1/d_{pix}$). Here, the sampling interval $d_{pix}$ is set to 0.044 $\mu m$.

$$d_{pix}=0.5/f_{Nyquist} \quad (14)$$

Accordingly, in the PC 20, which is a modulation control signal generation unit, a modulation control signal for scanning the sample 1 at the sampling intervals $d_{pix}$ calculated in the equation (14) is generated.

In step S6, a pinhole diameter $d_{PH}$ is set for the confocal stop 17. It is desired that the pinhole diameter $d_{PH}$ be set equal to or smaller than a Rayleigh diameter so as to record a super-resolution component, i.e., a frequency component that is larger than the cut-off frequency $f_{c,ex}$ in the spatial intensity distribution of the excitation light on a sample, with a high contrast.

In particular, an Airy disk diameter $d_{em}$ of the fluorescent spot on the sample 1 is calculated by using equation (15) below. Here, the Airy disk diameter $d_{em}$ is calculated as 0.44 $\mu m$. Then, a pinhole diameter $d_{PH}$ is calculated from the calculated Airy disk diameter $d_{em}$ by using equation (16) below. In equation (16), if a value equal to or smaller than 1 is applied to the ratio $\alpha$, the pinhole diameter $d_{PH}$ becomes equal to or smaller than a Rayleigh diameter. Here, it is assumed that, for example, ratio $\alpha$=0.5.

$$d_{em}=1.22\lambda_{em}/NA \quad (15)$$

$$d_{PH}=\alpha \times d_{em} \times M_{ob} \quad (16)$$

As the value of the ratio $\alpha$ becomes larger, it becomes necessary to increase the degree of intensification of a super-resolution frequency domain (superresolution component) in the emphasizing process with the use of a convolution filter CF, which will be described later. For this reason, if the value of the ratio $\alpha$ is too large, the noise in a superresolution image will tend to stand out. By contrast, when the value of the ratio $\alpha$ becomes smaller, the detection efficiency decreases, and the S/N ratio of the generated image data also decreases. For this reason, when the value of the ratio $\alpha$ is too small, the noise in a superresolution image will tend to stand out. Hence, it is desired that the ratio $\alpha$ be set to an optimal value inconsideration of the circumstances discussed above.

Figure 6:
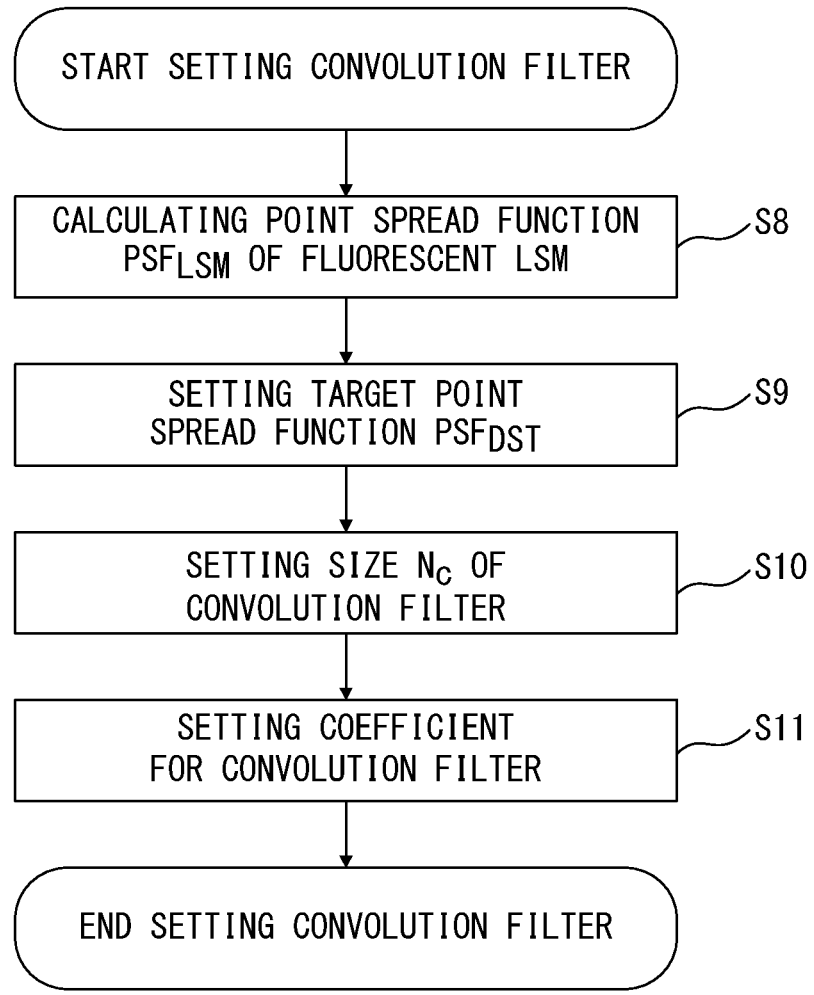
FIG. 6 is a flowchart of the processes of setting a convolution filter depicted in FIG. 5.
Figure 7:
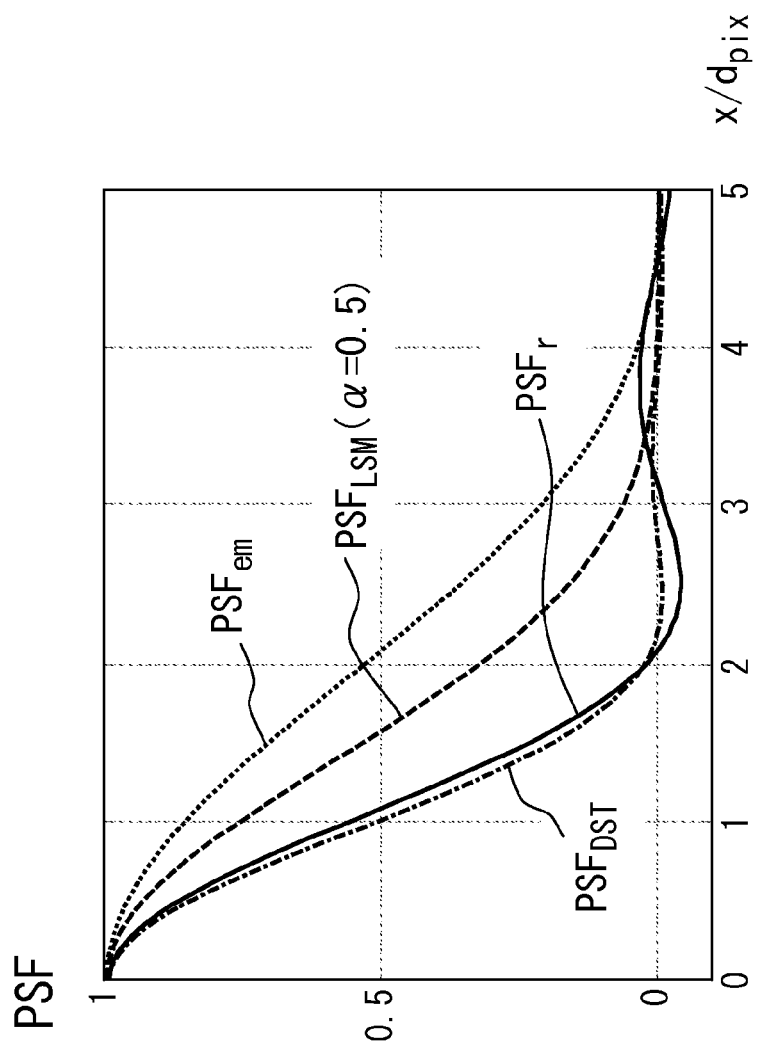
FIG. 7 illustrates the processes of setting a convolution filter depicted in FIG. 5.

In step S7, a digital convolution filter CF that is used by the PC 20 to emphasize a high-frequency component is set. The convolution filter will be described with reference to FIG. 6 and FIG. 7. FIG. 6 is a flowchart of the processes of setting a convolution filter (step S7), which is illustrated in FIG. 5. FIG. 7 illustrates the processes of setting the convolution filter illustrated in FIG. 5.

Firstly, in step S8, an actual Point Spread Function $PSF_{LSM}$ of a fluorescence LSM is calculated by using equation (1) (see the broken line in FIG. 7). As illustrated in FIG. 7, an actual Point Spread Function $PSF_{LSM}$ indicates a high image-forming capability compared with a Point Spread Function $PSF_{em}$ of a wide-field fluorescence microscope.

In step S9, a target Point Spread Function $PSF_{DST}$, which is obtained after performing an emphasizing process by a convolution filter CF, is set (see the alternate long and short dashed lines of FIG. 7). In the target Point Spread Function $PSF_{DST}$, for example, a virtual Point Spread Function in which the cut-off frequency $f_{DST}$ satisfies equation (17) below is set.

$$f_{ex}<f_{DST}<f_{ex}+f_{em} \quad (17)$$

Note that as the cut-off frequency $f_{DST}$ becomes larger, it becomes necessary for the degree of intensification of a superresolution frequency domain (super-resolution component) in the emphasizing process with the use of a convolution filter CF to become larger. For this reason, when the value of the cut-off frequency $f_{DST}$ is too large, the noise in a super-resolution image tends to stand out. Hence, it is desired that the cut-off frequency $f_{DST}$ be set to an optimal value in consideration of the circumstances discussed above.

Next, in step S10, the size $N_c$ of the convolution filter CF is set. Here, it is assumed that, for example, $N_c=7$. When the size $N_c$ of the convolution filter CF is large, the calculation cost (i.e., the time for calculation, the amount of memory to be used, etc.) also becomes large. Hence, it is desired that the size $N_c$ be set to be optimal in consideration of the superresolution characteristics of a superresolution image and in consideration of the calculation cost.

Finally, in step S11, a coefficient is set for a convolution filter CF. The coefficient of a convolution filter CF is calculated by numeral calculations with least squares so as to satisfy equation (18) below, and the calculated coefficient is set.

$$PSF_{LSM} \otimes CF \approx PSF_{DST} \quad (18)$$

An example of the result of calculating coefficients of a convolution filter CF where the ratio $\alpha=0.5$ is depicted as follows.

$$CF = \begin{bmatrix} -1.03 & 3.34 & -4.81 & 4.37 & -4.81 & 3.34 & -1.03 \\ 3.34 & -9.57 & 10.66 & -5.85 & 10.66 & -9.57 & 3.34 \\ -4.81 & 10.66 & -2.14 & -14.32 & -2.14 & 10.66 & -4.81 \\ 4.37 & -5.85 & -14.32 & 41.64 & -14.32 & -5.85 & 4.37 \\ -4.81 & 10.66 & -2.14 & -14.32 & -2.14 & 10.66 & -4.81 \\ 3.34 & -9.57 & 10.66 & -5.85 & 10.66 & -9.57 & 3.34 \\ -1.03 & 3.34 & -4.81 & 4.37 & -4.81 & 3.34 & -1.03 \end{bmatrix} \quad (19)$$

If the convolution filter CF calculated as above is used to perform an emphasizing process (convolution operation) on image data, as illustrated in FIG. 7, it becomes possible to obtain the image data of a superresolution image having a Point Spread Function $PSF_r$ that is approximately equal to a target Point Spread Function $PSF_{DST}$ (see the solid line in FIG. 7). Note that the coefficient of the calculated convolution filter CF varies depending on the ratio $\alpha$, i.e., the setting of a pinhole diameter.

Figure 8:
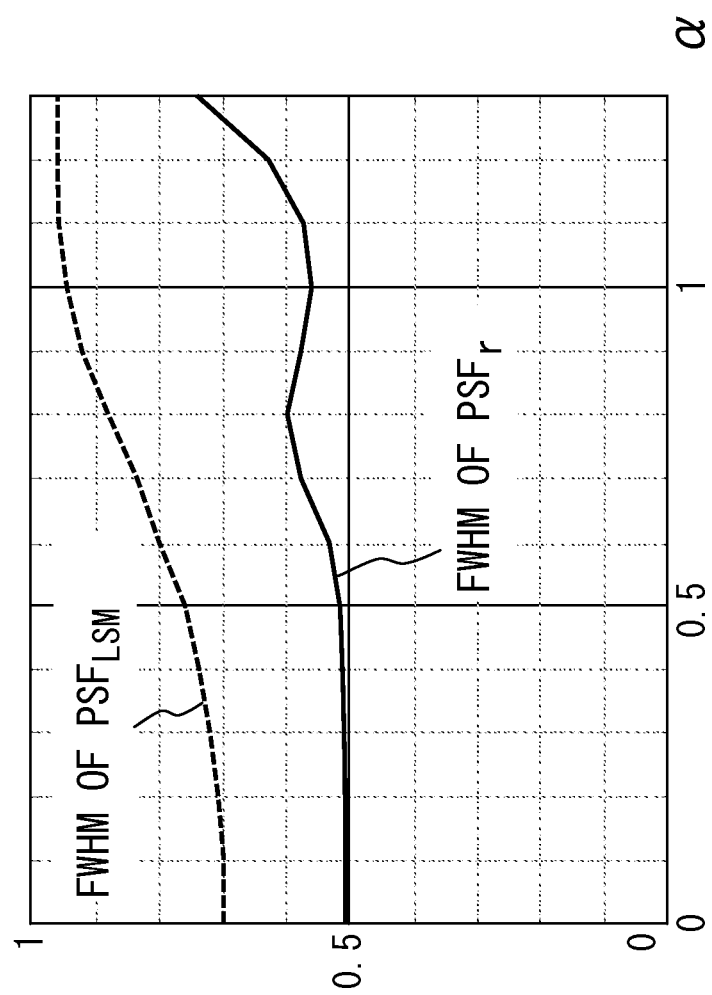
FIG. 8 is a diagram in which the FWHMs of Point Spread Functions before and after an emphasizing process is performed by a Fluorescence LSM according to the First Embodiment are compared with each other.

FIG. 8 illustrates the comparison between the FWHM of a Point Spread Function $PSF_{LSM}$ and the FWHM of a Point Spread Function $PSF_r$ before and after an emphasizing process is performed in the fluorescence LSM 10 according to the First Embodiment. The horizontal axis indicates the aforementioned ratio $\alpha$ of the aperture diameter of a confocal stop to the aforementioned Airy disk diameter, and the vertical axis indicates a ratio of the FWHMs of the Point Spread Functions with reference to that of a wide-field fluorescence microscope. The FWHM of the Point Spread Function $PSF_{LSM}$ obtained after an emphasizing process is performed in the fluorescence LSM 10 according to the First Embodiment is on the order of 0.5 to 0.8 times the FWHM of a Point Spread Function of a wide-field fluorescence microscope when the ratio $\alpha<1.2$. In other words, the fluorescence LSM 10 according to the First Embodiment has a superresolution on the order of 1.6 to 2 times larger than that of a wide-field fluorescence microscope when the ratio $\alpha<1.2$. Accordingly, the fluorescence LSM 10 may achieve a high superresolution without degradation in detection efficiency due to excessive reduction in the ratio $\alpha$.

The coefficient of the convolution filter CF may be adjusted depending on a wavelength of the excitation light 2 or a wavelength of the fluorescent light 3. The coefficient of the convolution filter CF may be adjusted depending on a numerical aperture on the emitting side of the objective lens 15. The coefficient of the convolution filter CF may be adjusted depending on the magnification at which an optical image of the sample 1 is projected to the confocal stop 17. Furthermore, the coefficient of the convolution filter CF may be adjusted depending on the Nyquist frequency of the image data $f_{Nyquist}$. Accordingly, the coefficient of the convolution filter CF may be optimized to a wavelength of the excitation light 2, a wavelength of the fluorescent light 3, a numerical aperture, a magnification, and a Nyquist frequency in the fluorescence LSM 10.

Moreover, the convolution filter CF may be a LoG (Laplacian of Gaussian) filter, which are widely used in the fields of image processing. Accordingly, the noise in a superresolution image may be effectively inhibited. When a numerical aperture of the objective lens 15 exceeds 0.5, as described as an example in the First Embodiment, in order to improve the calculation accuracy, a Point Spread Function may be calculated by applying the vector diffraction theory thereto.

When all types of settings including the setting of the convolution filter CF are completed, as illustrated in step S12 of FIG. 5, an image capturing process is performed by the fluorescence LSM 10. At this time, the galvano mirror 13 scans the sample 1 at sampling intervals $d_{pix}$ set in step S5. Accordingly, the image data containing a super-resolution component larger than the cut-off frequency $f_{c,ex}$ in the spatial intensity distribution of the excitation light 2 on the sample 1 is generated by the PC 20.

In step S13, an emphasizing process is performed by the PC 20 on the obtained image data by performing a convolution operation with the use of the convolution filter CF that is set in step S7. Accordingly, the image data of a superresolution image in which a super-resolution component larger than the cut-off frequency $f_{c,ex}$ in the spatial intensity distribution of the excitation light 2 on the sample 1 is emphasized is generated by the PC 20.

The image data of a superresolution image generated in step S13 is displayed on the monitor 22 in step S14. In step S15, whether or not the image capturing process should be continued is determined, and when it is determined that the image capturing process should be continued, the process returns to step S12 and the same processes are repeated. Accordingly, the video of the superresolution image is displayed on the monitor 22.

When the image capturing process terminates, the image data of a superresolution image generated in step S16 is stored in the storage device 21, and then the process terminates.

As described above, according to the fluorescence LSM 10 of the First Embodiment, a superresolution image on which a super-resolution component is visualized may be produced. In particular, the fluorescence LSM 10 may visualize a super-resolution component by performing an emphasizing process on the super-resolution components, which are not visualized in the conventional art. Due to the emphasizing process, as illustrated in FIG. 8, even if the pinhole diameter (aperture diameter) of the confocal stop 17 is extended to a diameter on the order of the Rayleigh diameter, a high superresolution may be achieved. For this reason, the fluorescence LSM 10 may achieve both a high utilization efficiency of light and a superresolution capability. Moreover, as it is possible to calculate from the characteristics of the known optical system the pinhole diameter (aperture diameter) or sampling intervals suitable for the generation of a superresolution image, operations such as obtaining an image in advance and adjusting the settings are not necessary in the fluorescence LSM 10, and thus the settings of the aperture diameter or sampling interval may be automated. Furthermore, as the emphasizing process is a simple convolution operation of a matrix, the emphasizing process may be completed in a short period of time. In other words, the PC 20 may perform the emphasizing process in real time in accordance with the generation of image data, and the fluorescence LSM 10 may display a superresolution image on the monitor 22 almost in real time after an image is captured.

As is apparent from equation (1), the excitation light that is distributed outside the convolution of the Point Spread Function $PSF_{em}$ in the detection wavelength on a sample plane and the transmission function PH of a pinhole do not contribute to the image forming process of an LSM. Accordingly, it is not always necessary for the excitation light to be condensed to one spot.

Second Embodiment

Figure 9:
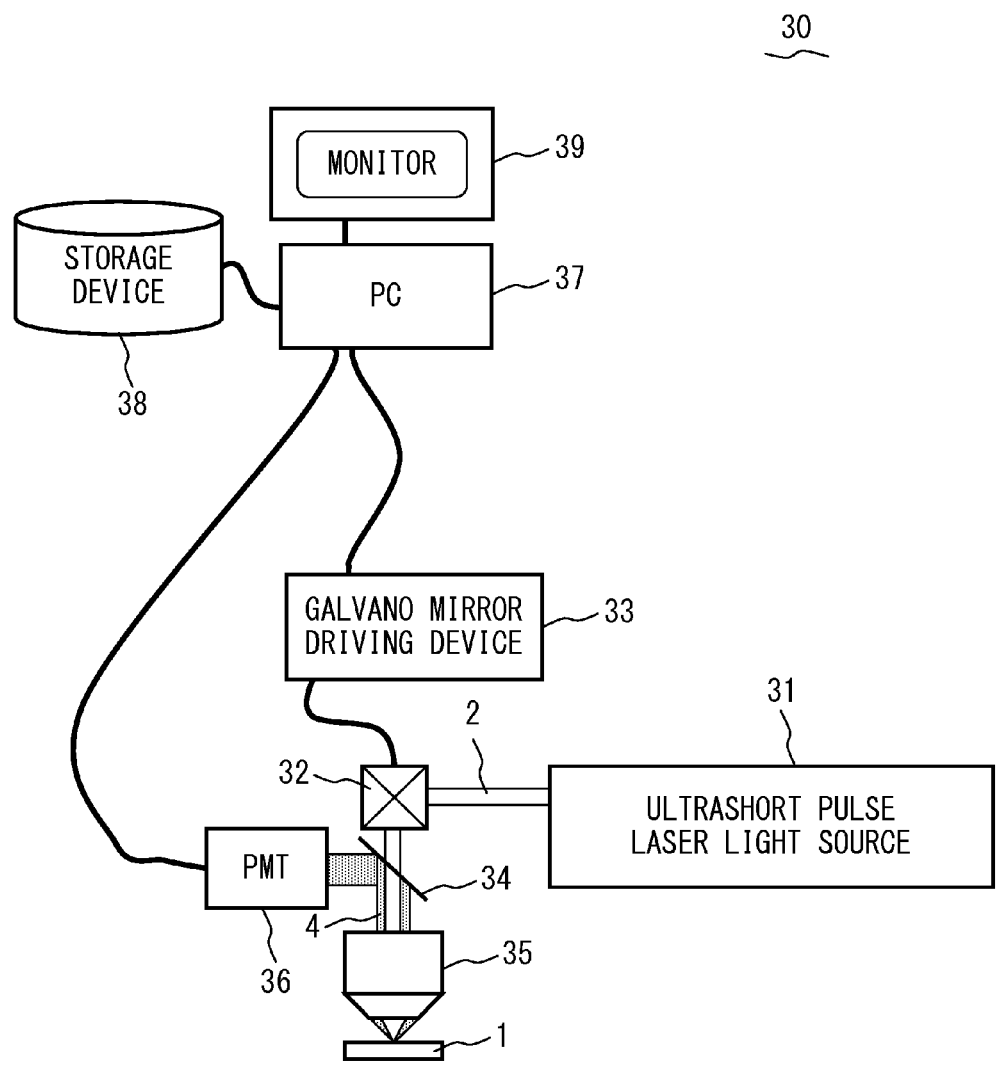
FIG. 9 illustrates an example of the configuration of a two-photon excitation microscope according to the Second Embodiment.

FIG. 9 illustrates an example of the configuration of a two-photon excitation microscope according to the Second Embodiment. A two-photon excitation microscope 30, which is illustrated in FIG. 9 as an example, is a sample observation apparatus that generates a superresolution image on which a superresolution component is visualized in a similar manner as the fluorescence LSM 10 according to the First Embodiment. The two-photon excitation microscope 30 includes: an ultrashort pulse laser light source 31 that emits an ultrashort pulse laser light as the excitation light 2; a galvano mirror 32 that scans the sample 1; a galvano mirror driving device 33 that drives the galvano mirror 32 according to a modulation control signal; a dichroic mirror 34 that allows the excitation light 2 to pass through and that reflects the two-photon fluorescent light 4 from the sample 1; an objective lens 35 that condenses the excitation light 2 onto the sample 1; a PMT detector 36 that detects the two-photon fluorescent light 4 (multi-photon fluorescent light) radiated from the sample 1 to generate a detection signal; a PC 37 that generates the image data of the sample 1 according to a modulation control signal and a detection signal; a storage device 38 that stores the image data of the sample 1; and a monitor 39 that displays the image data of the sample 1.

In contrast to the fluorescence LSM 10, the two-photon excitation microscope 30 may cause a confocal effect by using two-photon excitation. For this reason, the configuration of guiding fluorescent light (two-photon fluorescent light 4) to the PMT detector 36 is different from that of the fluorescence LSM 10. As a result, the image-forming formula of the two-photon excitation microscope 30 is different from that of the fluorescence LSM 10. In particular, an image-forming formula of the two-photon excitation microscope 30 is expressed as in equations (20) and (21).

$$PSF_{2p}(r) = PSF_{ex}^2(r) \tag{20}$$

$$MTF_{2p}(f) = MTF_{ex}(f) \otimes MTF_{ex}(f) \tag{21}$$

In equations (20) and (21) above, $PSF_{2p}$ and $MTF_{2p}$ indicate a Point Spread Function and a Modulation Transfer Function, respectively, which indicate the image-forming characteristics of the two-photon excitation microscope 30. $PSF_{ex}$ and $MTF_{ex}$ indicate a Point Spread Function of the excitation light spot on the sample 1 and a Modulation Transfer Function that is obtained by performing Fourier transformation on the Point Spread Function, respectively, both of which indicate the light condensing characteristics when the excitation light is condensed onto a sample plane. "r" is the distance from the optical axis, and indicates space coordinates of the sample position. "f" is a spatial frequency coordinate conjugate to "r". $PSF_{ex}$ and $MTF_{ex}$ are indicated by equations (3) and (5) above.

As illustrated in equations (20) and (21), the image-forming characteristics of the two-photon excitation microscope 30 depend on the Modulation Transfer Function $MTF_{ex}$ and the Point Spread Function $PSF_{ex}$, which are the light condensing characteristics when the excitation light is condensed onto a sample plane, but do not depend on the Modulation Transfer Function $MTF_{em}$ and the Point Spread Function $PSF_{em}$ of the detection wavelength (fluorescent wavelength). In this respect, the image-forming characteristics of the two-photon excitation microscope 30 are different from those of the fluorescence LSM 10 according to the First Embodiment.

The two-photon excitation microscope 30 is similar to the fluorescence LSM 10 in that the PC 37 generates a modulation control signal such that the Nyquist frequency of image data to be generated will be larger than the cut-off frequency in the spatial intensity distribution of the excitation light 2 on the sample 1, and performs image processing by emphasizing a high-frequency component that exceeds the cut-off frequency in the spatial intensity distribution of the excitation light 2 on the sample 1 included in the generated image data. In other words, in the two-photon excitation microscope 30 as well, in a similar manner to the fluorescence LSM 10, the PC 37 configures an image generation unit that generates the image data of the sample 1 and configures a modulation control signal generation unit that generates a modulation control signal, and also configures an image processing unit that emphasizes a high-frequency component. In a similar manner to the First Embodiment, the Nyquist frequency is compared with the cut-off frequency in consideration of the projection magnification of the sample image on the image plane. In particular, a converted amount obtained by adjusting one of the Nyquist frequency and the cut-off frequency with the projection magnification is compared with the other one of the Nyquist frequency and the cut-off frequency.

Figure 10:
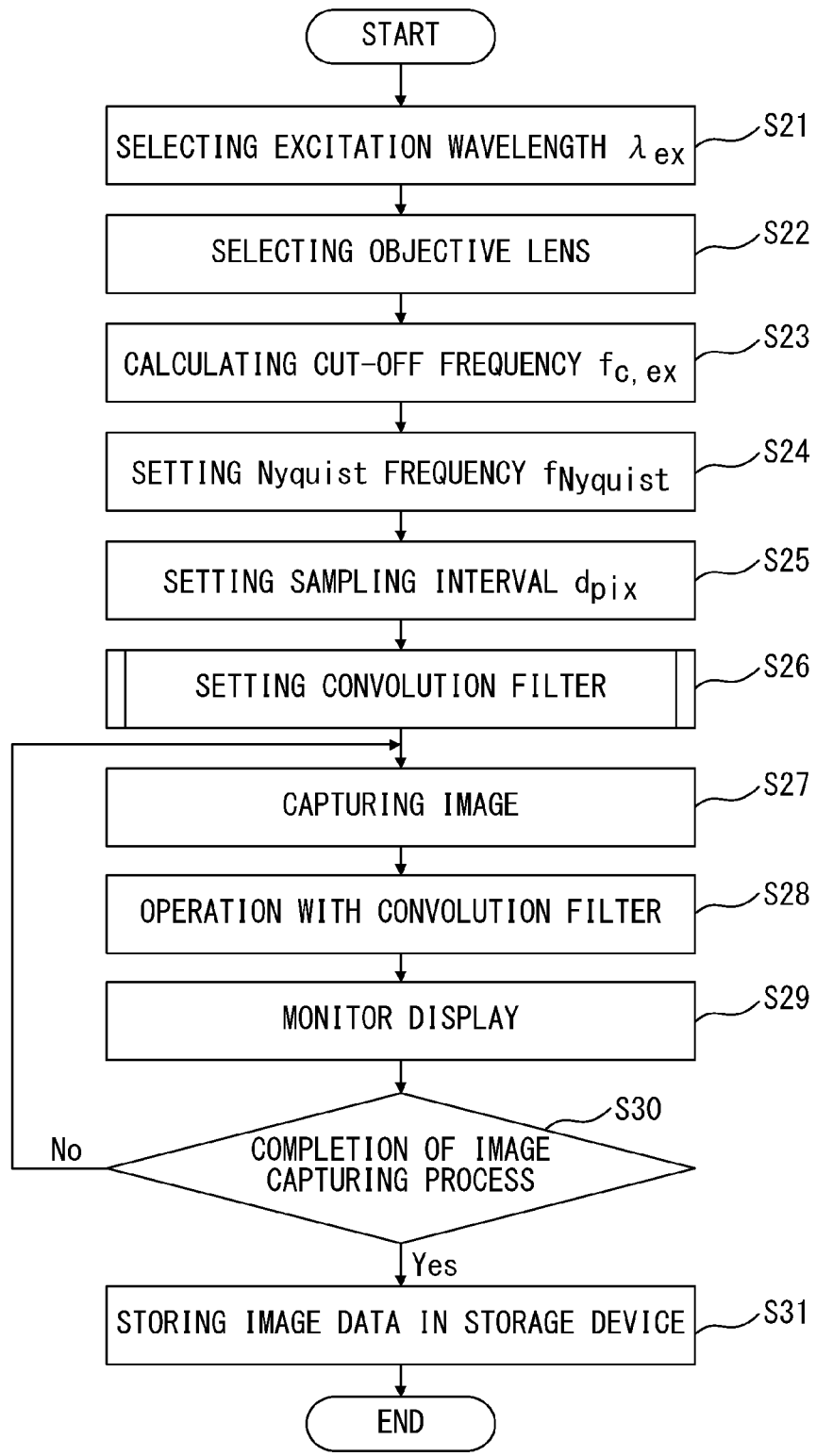
FIG. 10 is a flowchart illustrating the processes in which a two-photon excitation microscope according to the Second Embodiment generates a superresolution image.

FIG. 10 is a flowchart illustrating the processes of generating a superresolution image, which are performed by the two-photon excitation microscope according to the Second Embodiment. A method for generating a superresolution image by using the two-photon excitation microscope 30 will be described with reference to FIG. 10 in a specific manner.

Once the processes of generating a superresolution image are started, firstly, in step S21, a user selects an excitation wavelength $\lambda_{ex}$ to be used for observation, and the excitation wavelength $\lambda_{ex}$ is set to the two-photon excitation microscope 30. For example, if the ultrashort pulse laser light source 31 is a titanium sapphire laser (Ti: Sapphire Laser), the excitation wavelength is set to $\lambda_{ex}$=900 nm in step S21.

In step S22, the user selects the objective lens 35. For example, an objective lens in which the magnification is 25 and the numerical aperture is 1.05 is selected, and $M_{ob}$=25 and NA=1.05 are set to the two-photon excitation microscope 30.

In step S23, a cut-off frequency $f_{c,ex}$ in the spatial intensity distribution of the excitation light 2 on the sample 1 is calculated. Here, this cut-off frequency is calculated as $f_{c,ex}$=2.3 $\mu m^{-1}$ by using equation (9).

In step S24, the Nyquist frequency of the image data to being generated by the two-photon excitation microscope 30 is set. The Nyquist frequency of the image data $f_{Nyquist}$ is set to be larger than the cut-off frequency $f_{c,ex}$ in the spatial intensity distribution of the excitation light 2 on the sample 1 in order to record a super-resolution component. Here, for example, the Nyquist frequency of the image data $f_{Nyquist}$=4.6 $\mu m^{-1}$ calculated by an equation (22) below is set.

$$f_{Nyquist} = 2f_{c,ex} \tag{22}$$

Accordingly, a frequency component on the order of twice the cut-off frequency $f_{c,ex}$ in the spatial intensity distribution of the excitation light 2 on the sample 1 may be recorded.

For similar reasons to the First Embodiment, it is desired that the Nyquist frequency $f_{Nyquist}$ be equal to or larger than 1.5 times the cut-off frequency $f_{c,ex}$ and be four times the cut-off frequency $f_{c,ex}$ at most. Accordingly, the relationship between the Nyquist frequency of the image data $f_{Nyquist}$ and the cut-off frequency $f_{c,ex}$ is not limited to equation (22).

In step S25, sampling intervals at which the galvano mirror 32 scans the sample 1 are set according to the Nyquist frequency $f_{Nyquist}$ set in step S24. In particular, sampling intervals $d_{pix}$ are set to the value calculated by the aforementioned equation (14) such that the Nyquist frequency $f_{Nyquist}$ will be half the sampling frequency ($f_{pix}=1/d_{pix}$). Here, the sampling interval $d_{pix}$ is set to 0.11 μm.

In step S26, a convolution filter CF that is used for a high-frequency emphasizing process by the PC 37 is set. The detailed procedure for setting a convolution filter CF is similar to that of the fluorescence LSM 10 according to the First Embodiment. Note that, in the two-photon excitation microscope 30, a Point Spread Function $PSF_{DST}$ and a Modulation Transfer Function $MTF_{DST}$ that are indicated in equations (23) and (24) below are set to targets, and a convolution filter CF is calculated and set so as to satisfy equation (25) below. In this respect, the procedure in step 26 is different from that of the fluorescence LSM 10 according to the First Embodiment. In other words, in the two-photon excitation microscope 30, a Point Spread Function of a wide-field fluorescent image where the cut-off frequency is equal to that of the two-photon fluorescent image is set to the target Point Spread Function $PSF_{DST}$.

$$PSF_{DST}(r) \equiv PSF_{ex}(2r) \quad (23)$$

$$MTF_{DST}(f) \equiv MTF_{ex}\left(\frac{f}{2}\right) \quad (24)$$

$$PSF_{2p} \otimes CF \cong PSF_{DST} \quad (25)$$

Figure 11:
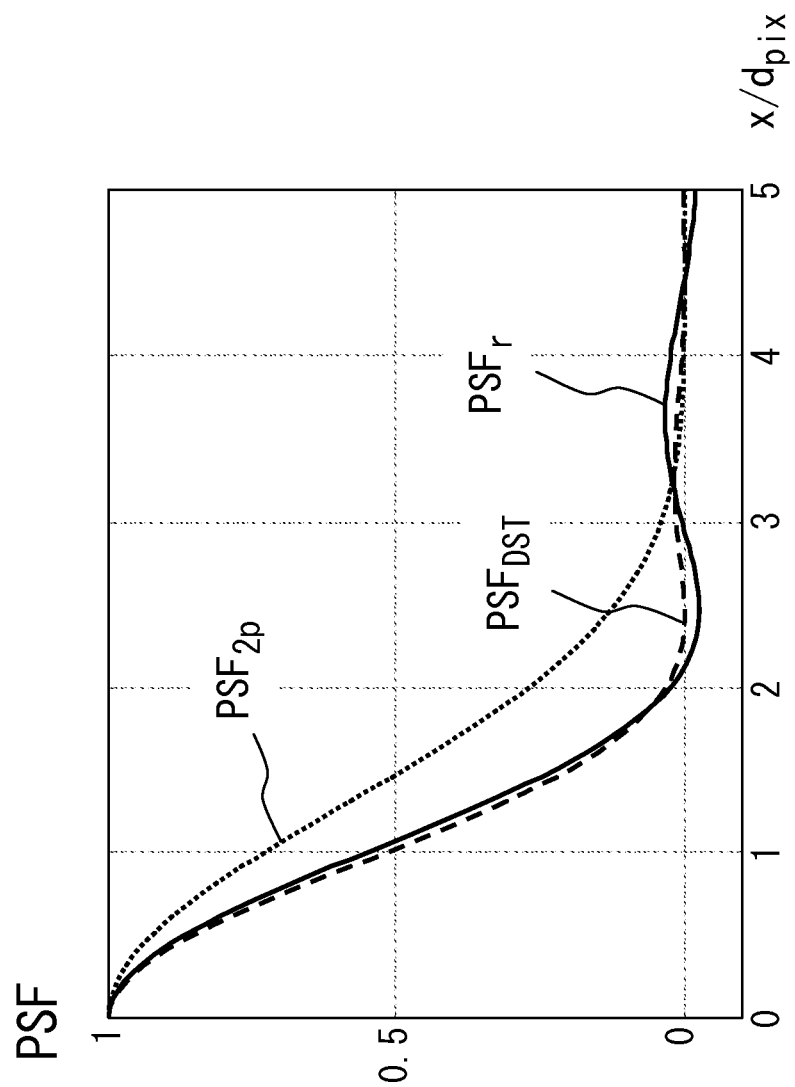
FIG. 11 illustrates an example of the Point Spread Functions before and after an emphasizing process is performed by a two-photon excitation microscope according to the Second Embodiment and illustrates the target Point Spread Function after an emphasizing process is performed.
Figure 12:
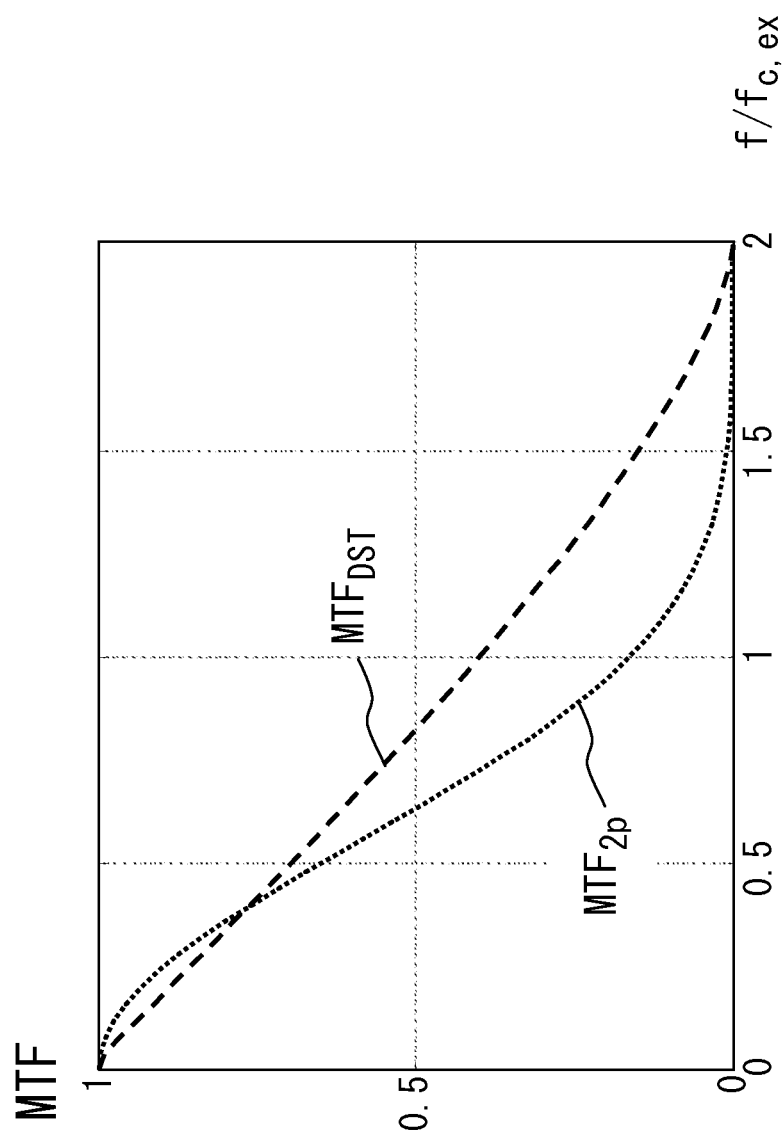
FIG. 12 illustrates an example of the Modulation Transfer Function before an emphasizing process is performed by a two-photon excitation microscope according to the Second Embodiment and illustrates the target Modulation Transfer Function after an emphasizing process is performed.

In FIG. 11, a Point Spread Function $PSF_{2p}$ before an emphasizing process is performed in the two-photon excitation microscope 30 is compared with a target Point Spread Function $PSF_{DST}$ after an emphasizing process is performed in the two-photon excitation microscope 30, and the Point Spread Functions $PSF_{2p}$ and $PSF_{DST}$ are indicated by a dotted line and a broken line, respectively. In FIG. 12, a Modulation Transfer Function $MTF_{2p}$ before an emphasizing process is performed in the two-photon excitation microscope 30 is compared with a target Modulation Transfer Function $MTF_{DST}$ after an emphasizing process is performed in the two-photon excitation microscope 30, and the Modulation Transfer Functions $MTF_{2p}$ and $MTF_{DST}$ are indicated by a dotted line and a broken line, respectively.

An example of the result of calculation of the coefficient of a convolution filter CF is given below.

$$CF = \begin{bmatrix} -0.43 & 1.40 & -2.05 & 1.82 & -2.05 & 1.40 & -0.43 \\ 1.40 & -4.16 & 5.00 & -2.89 & 5.00 & -4.16 & 1.40 \\ -2.05 & 5.00 & -2.51 & -4.66 & -2.51 & 5.00 & -2.05 \\ 1.82 & -2.89 & -4.66 & 17.52 & -4.66 & -2.89 & 1.82 \\ -2.05 & 5.00 & -2.51 & -4.66 & -2.51 & 5.00 & -2.05 \\ 1.40 & -4.16 & 5.00 & -2.89 & 5.00 & -4.16 & 1.40 \\ -0.43 & 1.40 & -2.05 & 1.82 & -2.05 & 1.40 & -0.43 \end{bmatrix} \quad (26)$$

By performing an emphasizing process on the image data with the use of the convolution filter CF calculated as above, as illustrated in FIG. 11, the image data of a superresolution image having a Point Spread Function $PSF_r$ that is approximately equal to the target Point Spread Function $PSF_{DST}$ may be obtained (see solid line in FIG. 11).

When all types of settings including the setting of the convolution filter CF are completed, an image capturing process is performed by the two-photon excitation microscope 30 (step S27), and an emphasizing process is performed on the obtained image data by using the convolution filter CF (step S28). Then, the superresolution image generated by the convolution process is displayed on a monitor (step S29). Moreover, the video of the superresolution image is displayed by repeating these processes (steps S27 to S29) until the image capturing process terminates (step S30). When the image capturing process terminates, the image data of the superresolution image is stored in the storage device 21, and the processes terminate (step S31).

As described above, it is possible to generate a superresolution image on which a superresolution component is visualized by using the two-photon excitation microscope 30 according to the Second Embodiment, and thus advantageous effects that are similar to those of the fluorescence LSM 10 according to the First Embodiment may be obtained.

In the Second Embodiment, the two-photon excitation microscope 30 is used as a sample observation apparatus, but other kinds of multi-photon microscopes may generate a superresolution image by performing processes similar to the processes of generating a superresolution image that are illustrated in the flowchart of FIG. 10.

Third Embodiment

Figure 13:
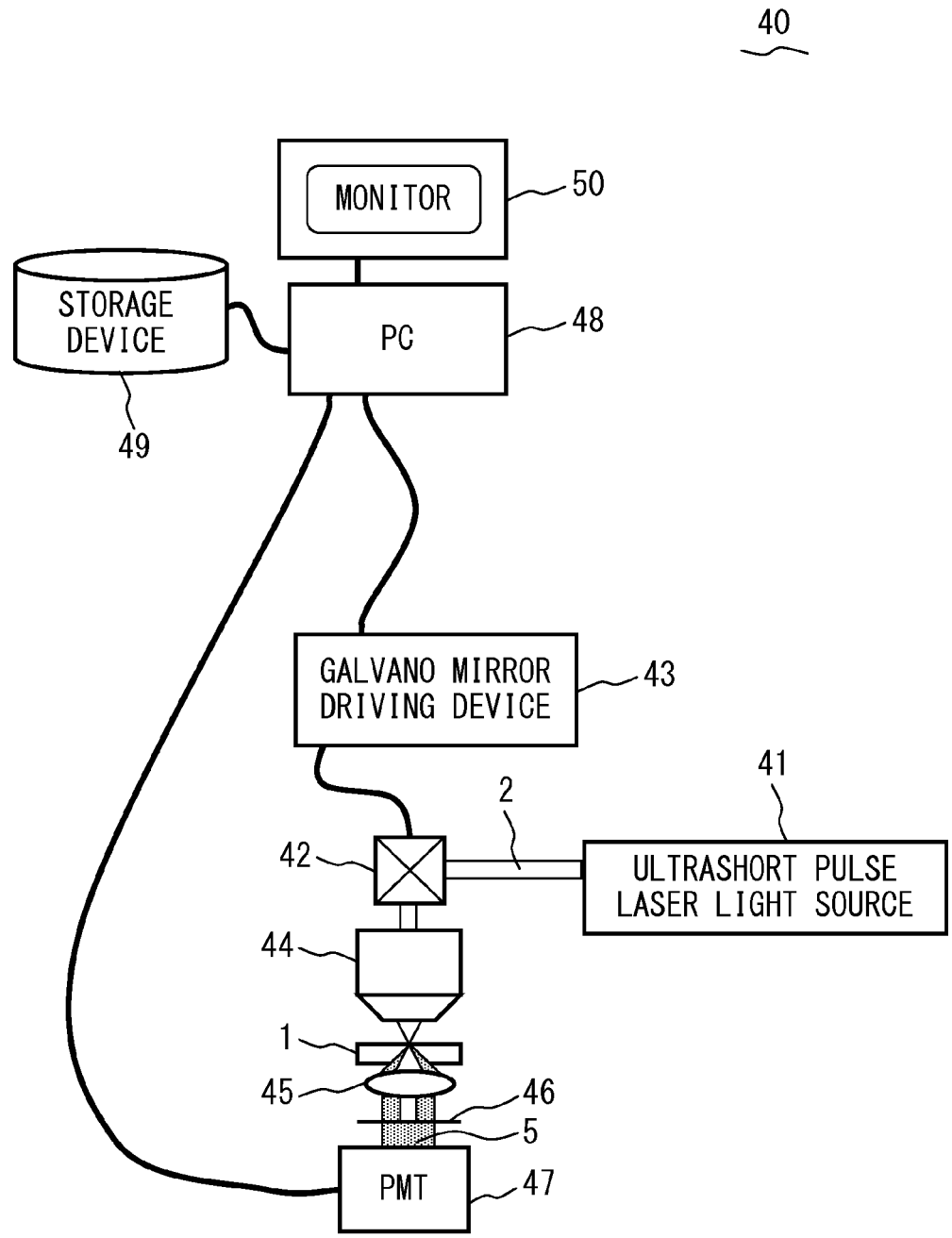
FIG. 13 illustrates an example of the configuration of a Second Harmonic Generation (SHG) microscope according to the Third Embodiment.

FIG. 13 illustrates an example of the configuration of a Second Harmonic Generation (SHG) microscope according to the Third Embodiment. The SHG microscope 40 of FIG. 13 is a sample observation apparatus that generates a superresolution image on which a super-resolution component is visualized, in a similar manner to the fluorescence LSM 10 according to the First Embodiment. The SHG microscope 40 includes: an ultrashort pulse laser light source 41 that emits an ultrashort pulse laser light, i.e., the excitation light 2; a galvano mirror 42 that scans the sample 1; a galvano mirror driving device 43 that drives the galvano mirror 42 according to a modulation control signal; an objective lens 44 that condenses the excitation light 2 onto the sample 1; a lens 45 that condenses an SHG light 5 generated at the sample 1; a barrier filter 46 that blocks the excitation light 2 that passed through the sample 1; a PMT detector 47 that detects the SHG light 5 (higher-order harmonics) generated at the sample 1 to generate a detection signal; a PC 48 that generates the image data of the sample 1 according to a modulation control signal and a detection signal; a storage device 49 that stores the image data of the sample 1; and a monitor 50 that displays the image data of the sample 1. Note that the SHG light 5 that is detected in the SHG microscope 40 is not a fluorescent light but a coherent light. Hence, the PMT detector 47 is arranged in the optical path of the transmitted light.

The SHG microscope 40 is similar to the fluorescence LSM 10 and the two-photon excitation microscope 30 in that the PC 48 generates a modulation control signal such that the Nyquist frequency of image data to be generated will be larger than the cut-off frequency in the spatial intensity distribution of the excitation light 2 on the sample 1, and performs image processing by emphasizing a high-frequency component that exceeds the cut-off frequency in the spatial intensity distribution of the excitation light 2 on the sample 1 included in the generated image data. In other words, in the SHG microscope 40 as well, the PC 48 configures an image generation unit that generates the image data of the sample 1 and configures a modulation control signal generation unit that generates a modulation control signal, and also configures an image processing unit that emphasizes a high-frequency component. In a similar manner to the First Embodiment, the Nyquist frequency is compared with the cut-off frequency in consideration of the projection magnification of the sample image on the image plane. In particular, a converted amount obtained by adjusting one of the Nyquist frequency and the cut-off frequency with the projection magnification is compared with the other one of the Nyquist frequency and the cut-off frequency.

The flowchart of the processes of generating a superresolution image by using the SHG microscope 40 is similar to that of the two-photon excitation microscope 30 according to the Second Embodiment. Hence, detailed description of it will be omitted.

As described above, it is possible to generate a superresolution image on which a super-resolution component is visualized by using the SHG microscope 40 according to the Third Embodiment, and thus advantageous effects that are similar to those of the fluorescence LSM 10 according to the First Embodiment or the two-photon excitation microscope 30 according to the Second Embodiment may be obtained.

In the Third Embodiment, the SHG microscope 40 is used as a sample observation apparatus, but other kinds of higher-order harmonic generation microscopes such as a Third Harmonic Generation (THG) microscope may generate a super-resolution image in similar processes of generating a superresolution image.

Fourth Embodiment

FIG. 14 illustrates an example of the configuration of a coherent anti-Stokes Raman scattering (CARS) microscope according to the Fourth Embodiment. The CARS microscope 60 of FIG. 14 is a sample observation apparatus that generates a superresolution image on which a super-resolution component is visualized, in a similar manner to the fluorescence LSM 10 according to the First Embodiment. The CARS microscope 60 includes: a pump light laser light source 61 that emits a pump light 6, i.e., an excitation light; a Stokes light laser light source 62 that emits a Stokes light 7, i.e., an excitation light in which the wavelength is different from that of the pump light 6; a mirror 63; a dichroic mirror 64 that allows the pump light 6 to pass through and that reflects the Stokes light 7; a galvano mirror 65 that scans the sample 1; a galvano mirror driving device 66 that drives the galvano mirror 65 according to a modulation control signal; an objective lens 67 that condenses excitation lights including two different wavelength components (pump light 6, Stokes light 7) onto the sample 1; a lens 68 that condenses a CARS light 8, i.e., anti-Stokes components included in a Raman scattering light from the sample 1; a barrier filter 69 that blocks an excitation light that passed through the sample 1; a PMT detector 70 that detects the CARS light 8 to generate a detection signal; a PC 71 that generates the image data of the sample 1 according to a modulation control signal and a detection signal; a storage device 72 that stores the image data of the sample 1; and a monitor 73 that displays the image data of the sample 1. Note that the CARS light 8 that is detected in the CARS microscope 60 is not a fluorescent light but a coherent light. Hence, the PMT detector 70 is arranged in the optical path of transmitted light.

The CARS microscope 60 causes the CARS light 8 by means of three-photon excitation with two photons of the pump light 6 and a single photon of the Stokes light 7. In particular, an image-forming formula of the CARS microscope 60 is expressed as in equations (27) and (28) below.

$$PSF_{CARS}(r) = PSF_{pump}^2(r) \cdot PSF_{Stokes}(r) \quad (27)$$

$$MTF_{CARS}(f) = MTF_{pump}(f) \otimes MTF_{pump}(f) \otimes MTF_{Stokes}(f) \quad (28)$$

In equations (27) and (28) above, $PSF_{CARS}$ and $MTF_{CARS}$ indicate a Point Spread Function that indicates the image-forming characteristics of the CARS microscope 60 and a Modulation Transfer Function that is obtained by performing Fourier transformation on the Point Spread Function, respectively. $PSF_{pump}$ and $MTF_{pump}$ indicate a Point Spread Function of the pump light spot on the sample 1 and a Modulation Transfer Function that is obtained by performing Fourier transformation on the Point Spread Function, respectively, both of which indicate light condensing characteristics when the pump light is condensed onto a sample plane. $PSF_{Stokes}$ and $MTF_{Stokes}$ indicate a Point Spread Function of the Stokes light spot on the sample 1 and a Modulation Transfer Function that is obtained by performing Fourier transformation on the Point Spread Function, respectively, both of which indicate light condensing characteristics when the Stokes light is condensed onto a sample plane. "r" is the distance from the optical axis, and indicates space coordinates of the sample position. "f" is a spatial frequency coordinate conjugate to "r".

Accordingly, assuming that wavelength of the pump light 6 is $\lambda_{pump}$ and a wavelength of the Stokes light 7 is $\lambda_{Stokes}$, a cut-off frequency in the spatial intensity distribution $f_{CARS}$ of the obtained CARS microscope image is expressed as in equation (29) below.

$$f_{CARS} = 2f_{pump} + f_{Stokes} \quad (29)$$

Here, a cut-off frequency $f_{pump}$ of the pump light 6 and a cut-off frequency $f_{Stokes}$ of the Stokes light 7 are expressed as in equations (30) and (31) below, respectively.

$$f_{pump} = \frac{2NA}{\lambda_{pump}} \quad (30)$$

$$f_{Stokes} = \frac{2NA}{\lambda_{Stokes}} \quad (31)$$

The CARS microscope 60 is similar to the fluorescence LSM 10 in that the PC 71 generates a modulation control signal such that the Nyquist frequency of image data to be generated will be larger than the cut-off frequency in the spatial intensity distribution of the excitation light 2 on the sample 1, and performs image processing by emphasizing a high-frequency component that exceeds the cut-off frequency in the spatial intensity distribution of the excitation light 2 on the sample 1 included in the generated image data. In other words, in the CARS microscope 60 as well, in a similar manner to the fluorescence LSM 10, the PC 71 configures an image generation unit that generates the image data of the sample 1 and configures a modulation control signal generation unit that generates a modulation control signal, and also configures an image processing unit that emphasizes a high-frequency component. In a similar manner to the First Embodiment, the Nyquist frequency is compared with the cut-off frequency in consideration of the projection magnification of the sample image on the image plane. In particular, a converted amount obtained by adjusting one of the Nyquist frequency and the cut-off frequency with the projection magnification is compared with the other one of the Nyquist frequency and the cut-off frequency.

Figure 15:
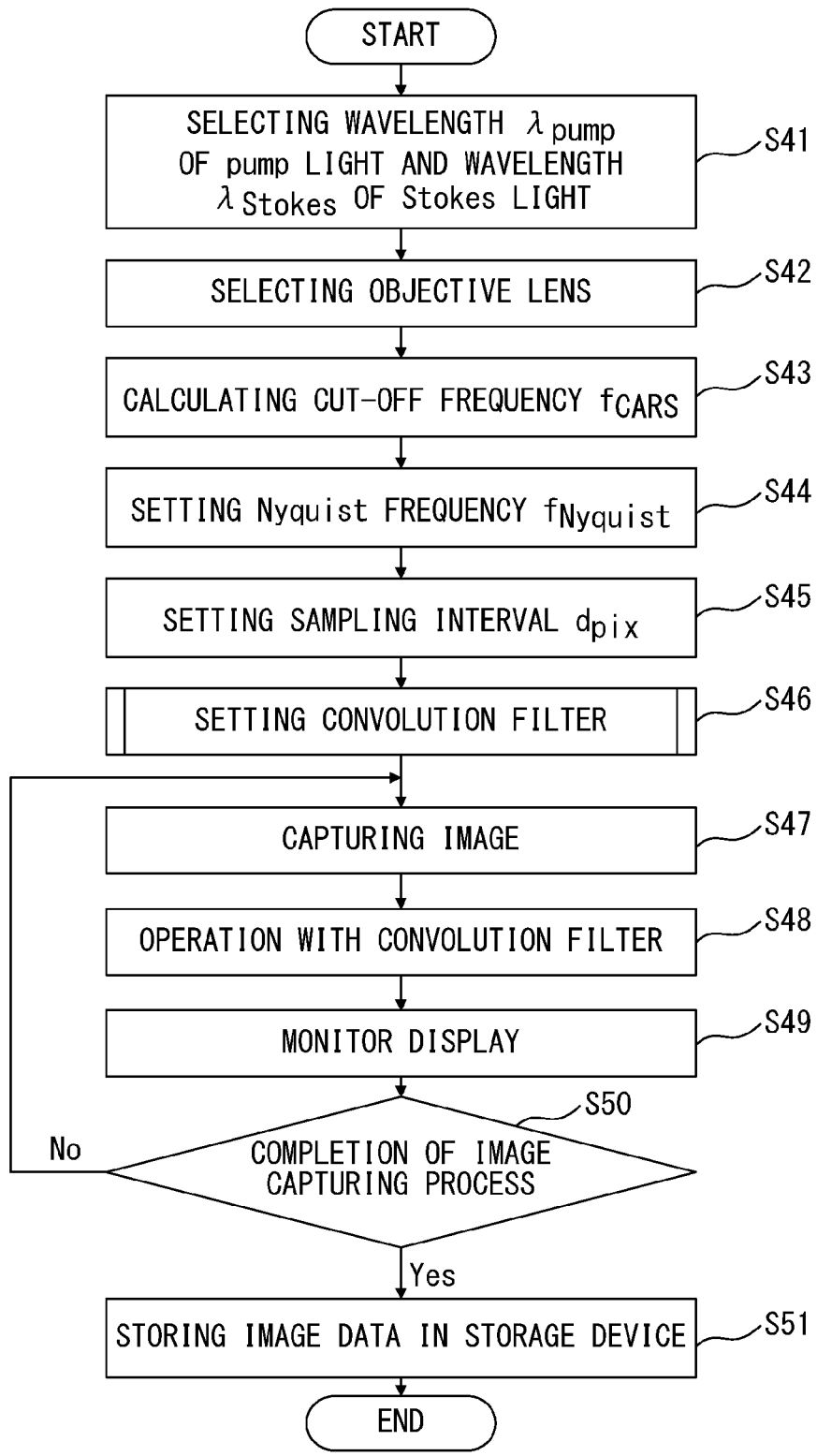
FIG. 15 is a flowchart illustrating the processes in which a CARS microscope according to the Fourth Embodiment generates a superresolution image.

FIG. 15 is a flowchart illustrating the processes of generating a superresolution image, which are performed by the CARS microscope according to the Fourth Embodiment. A method for generating a superresolution image by using the CARS microscope 60 will be described with reference to FIG. 15 in a specific manner.

Once the processes of generating a superresolution image are started, firstly, in step S41, a user selects a wavelength $\lambda_{pump}$ of the pump light 6 and a wavelength $\lambda_{Stokes}$ of the Stokes light 7 to be used for observation, and the wavelength $\lambda_{pump}$ of the pump light 6 and the wavelength $\lambda_{Stokes}$ of the Stokes light 7 are set to the CARS microscope 60. For example, if a lipid is to be observed by the CARS microscope 60, in step S41, the wavelengths of the pump light 6 and Stokes light 7 are set to $\lambda_{pump}$=711 nm and $\lambda_{Stokes}$=839 nm, respectively.

In step S42, a user selects the objective lens 67. For example, an objective lens in which the magnification is 60 and the numerical aperture is 1.2 is selected, and $M_{ob}$=60 and NA=1.2 are set to the CARS microscope 60.

In step S43, a cut-off frequency $f_{CARS}$ in the spatial intensity distribution of the excitation light on the sample 1 is calculated. Here, this cut-off frequency is calculated as $f_{CARS}$=9.6 $\mu m^{-1}$ by using equation (29).

As indicated in equations (29) to (31), the cut-off frequency $f_{CARS}$ in the spatial intensity distribution of the excitation light on the sample 1 is determined by a diffraction limit that is calculated from wavelengths $\lambda_{pump}$ and $\lambda_{Stokes}$ of the excitation light (pump light 6, Stokes light 7) and a numerical aperture NA on the emitting side (on the sample 1 side) of the objective lens 67.

In step S44, the Nyquist frequency of the image data to being generated by the CARS microscope 60 is set. The Nyquist frequency of the image data $f_{Nyquist}$ is set to be larger than the cut-off frequency in the spatial intensity distribution of the pump light and Stokes light on the sample 1 in order to record a super-resolution component. Here, for example, the Nyquist frequency of the image data $f_{Nyquist}$=9.6 $\mu m^{-1}$ calculated by equation (32) below is set.

$$f_{Nyquist} = f_{CARS} \quad (32)$$

In step S45, sampling intervals at which the galvano mirror 65 scans the sample 1 are set according to the Nyquist frequency $f_{Nyquist}$ set in step S44. In particular, sampling intervals $d_{pix}$ are set to the value calculated by the aforementioned equation (14) such that the Nyquist frequency $f_{Nyquist}$ will be half the sampling frequency ($f_{pix}$=1/$d_{pix}$). Here, the sampling interval $d_{pix}$ is set to 0.052 $\mu$m.

In step S46, a convolution filter CF that is used for a high-frequency emphasizing process by the PC 71 is set. The detailed procedure for setting is similar to that of the fluorescence LSM 10 according to the First Embodiment. Note that, in the CARS microscope 60, as a target Point Spread Function $PSF_{DST}$ obtained after an emphasizing process is performed by a convolution filter CF, for example, a virtual Point Spread Function of which the cut-off frequency $f_{DST}$ satisfies equation (33) below is set.

$$f_{DST} < 2f_{pump} + f_{Stokes} \quad (33)$$

When all types of settings including the setting of the convolution filter CF are completed, an image capturing process is performed by the CARS microscope 60 (step S47), and an emphasizing process is performed on the obtained image data by using the convolution filter CF (step S48). Then, the superresolution image generated by the convolution process is displayed on a monitor (step S49). Moreover, the video of the superresolution image is displayed by repeating these processes (steps S47 to S49) until the image capturing process terminates (step S50). When the image capturing process terminates, the image data of the superresolution image is stored in the storage device 72 (step S51), and the processes terminate.

As described above, it is possible to generate a superresolution image on which a super-resolution component is visualized by using the CARS microscope 60 according to the Fourth Embodiment, and thus advantageous effects that are similar to those of the fluorescence LSM 10 according to the First Embodiment, the two-photon excitation microscope 30 according to Second Embodiment, or the SHG microscope 40 according to the Third Embodiment may be obtained.

In the Fourth Embodiment, the CARS microscope 60 is used as a sample observation apparatus, but other kinds of microscopes, for example, a microscope in which a sample is observed by exciting the sample with an excitation light including two different wavelength components and by detecting the light emission caused by Four-Wave Mixing at the sample, may generate a superresolution image in similar processes of generating a superresolution image.

What is claimed is:

1. A sample observation apparatus comprising:
   an excitation light irradiation unit to irradiate a sample with an excitation light;
   an excitation light modulation unit to modulate a spatial intensity distribution of the excitation light on the sample;
   an excitation light modulation control unit to control the excitation light modulation unit according to a modulation control signal;
   a photo detection unit to detect light emission from the sample caused by irradiation with the excitation light to generate a detection signal;
   an image generation unit to generate image data of the sample according to the modulation control signal and the detection signal;
   a modulation control signal generation unit to generate the modulation control signal such that a Nyquist frequency of the image data will be larger than a cut-off frequency in the spatial intensity distribution of the excitation light on the sample; and
   an image processing unit to emphasize a high-frequency component that exceeds the cut-off frequency included in the image data.

2. The sample observation apparatus according to claim 1, wherein
   the excitation light irradiation unit includes a light condensing unit to condense at least a portion of the excitation light onto the sample, and
   the excitation light modulation unit is a scanning unit that scans the sample by moving a light-condensing position to which the light condensing unit condenses the excitation light.

3. The sample observation apparatus according to claim 2, wherein
   the modulation control signal generation unit generates the modulation control signal such that the Nyquist frequency of the image data will be equal to or larger than 1.5 times the cut-off frequency in the spatial intensity distribution of the excitation light on the sample.

4. The sample observation apparatus according to claim 2, wherein
   the modulation control signal generation unit generates the modulation control signal such that the Nyquist frequency of the image data will be equal to or smaller than four times the cut-off frequency in the spatial intensity distribution of the excitation light on the sample.

5. The sample observation apparatus according to claim 2, wherein
the cut-off frequency in the spatial intensity distribution of the excitation light is determined by a diffraction limit that is calculated from a wavelength of the excitation light and a numerical aperture on an emission side of the light condensing unit.

6. The sample observation apparatus according to claim 2, wherein
the Nyquist frequency of the image data is determined by sampling intervals at which the scanning unit scans the sample.

7. The sample observation apparatus according to claim 2, further comprising
a confocal stop that configures an aperture at an optically conjugate position with a light-condensing position of the light condensing unit.

8. The sample observation apparatus according to claim 7, wherein
an aperture diameter of the confocal stop is equal to or smaller than a Rayleigh diameter.

9. The sample observation apparatus according to claim 2, wherein
the image processing unit emphasizes the high-frequency component by using a digital convolution filter.

10. The sample observation apparatus according to claim 9, wherein
a coefficient of the digital convolution filter is adjusted in accordance with a wavelength of the excitation light.

11. The sample observation apparatus according to claim 9, wherein
a coefficient of the digital convolution filter is adjusted in accordance with a wavelength of the light emission.

12. The sample observation apparatus according to claim 9, wherein
a coefficient of the digital convolution filter is adjusted in accordance with a numerical aperture on an emission side of the light condensing unit.

13. The sample observation apparatus according to claim 9, wherein
a coefficient of the digital convolution filter is adjusted in accordance with a magnification at which an optical image of the sample is projected onto a light-receptive plane of the photo detection unit.

14. The sample observation apparatus according to claim 9, wherein
a coefficient of the digital convolution filter is adjusted in accordance with a Nyquist frequency of the image data.

15. The sample observation apparatus according to claim 1, wherein
the light emission non-linearly depends on irradiation strength of the excitation light on the sample.

16. The sample observation apparatus according to claim 15, wherein
the light emission is a multi-photon fluorescent light generated at the sample.

17. The sample observation apparatus according to claim 15, wherein
the light emission is a higher-order harmonics from the sample.

18. The sample observation apparatus according to claim 15, wherein
the excitation light includes two different wavelength components, and
the light emission includes anti-Stokes components included in a Raman scattering light from the sample.

19. The sample observation apparatus according to claim 15, wherein
the excitation light includes two or more different wavelength components, and
the light emission is caused by Four-Wave Mixing at the sample.

20. The sample observation apparatus according to claim 1, wherein
the image processing unit processes the image data in real time in accordance with the image data generated by the image generation unit.

* * * * *